(12) United States Patent
Bickenbach et al.

(10) Patent No.: US 6,927,060 B2
(45) Date of Patent: Aug. 9, 2005

(54) METHODS TO PREPARE AND USE EPIDERMAL STEM CELLS

(75) Inventors: Jackie R. Bickenbach, Iowa City, IA (US); Martine Dunnwald, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/820,198

(22) Filed: Mar. 28, 2001

(65) Prior Publication Data

US 2002/0045258 A1 Apr. 18, 2002

Related U.S. Application Data

(60) Provisional application No. 60/192,754, filed on Mar. 28, 2000.

(51) Int. Cl.[7] ................................................ C12N 5/00
(52) U.S. Cl. ........................ 435/325; 435/366; 435/383
(58) Field of Search ............................... 435/325, 366, 435/383

(56) References Cited

U.S. PATENT DOCUMENTS

| | | | | |
|---|---|---|---|---|
| 4,812,394 | A | * | 3/1989 | Dolbeare et al. |
| 5,202,230 | A | * | 4/1993 | Kamentsky |
| 5,423,778 | A | * | 6/1995 | Eriksson et al. |
| 5,639,618 | A | * | 6/1997 | Gay |
| 5,686,307 | A |   | 11/1997 | Wille, Jr. |
| 5,827,742 | A | * | 10/1998 | Scadden |
| 5,843,635 | A | * | 12/1998 | Sclossman et al. |
| 5,939,282 | A | * | 8/1999 | Harman et al. |
| 6,007,996 | A | * | 12/1999 | McNamara et al. |
| 6,132,979 | A | * | 10/2000 | Murakami |

FOREIGN PATENT DOCUMENTS

WO    WO-99/47644    9/1999

OTHER PUBLICATIONS

Bickenbach, Jackie R., et al. ,"Selection and Extended Growth of Murine Epidermal Stem Cells in Culture", *Experimental Cell Research, 244*, (1998), 184–195.
Bickenbach, J.R."A Novel Sorting Method Yields a Pure Population of Viable Stem Cells which Reforms a Complete Epidermis with Long–arm Recombinant Gene Expression", *Journal of Investigative Dermatology, 112*, Abstract No. 048, 60th Annual Meeting of the Society for Investigative Dermatology, Chicago IL,(Apr., 1999), 1 page.
Bickenbach, Jackie R., et al. ,"Transduction of a Preselected Population of Human Epidermal Stem Cells: Consequences for Gene Therapy", *Proceedings of the Association of American Physicians, 111*, Thematic Review Series VI: Skin Gene Therapy,(1999),184–189.
Dunnwald, M., et al. ,"Isolating a Pure Population of Epidermal Stem Cells for Use in Tissue Engineering", *Experimental Dermatology, 10*, (2001),45–54.

Lindberg, K. et al., "Three district keratinocyte subtypes identified in human oral epithelium by their patterns of keratin expression in culture and in xenografts", *Differentation, 45*, (1990), 230–241.
Bickenbach, J. R., "A novel sorting method yields a pure population of viable stem cells which reforms a complete epidermis with long–term recombinant gene expression", *Abstracts of the 60th Annual Meeting of The Society for Investigative Dermatology*, Chicago, May 5–9, 1999, Published in the Journal of Investigative Dermatology, vol. 112, No. 4 (Apr. 1999), 2 pages.
Bickenbach, J. R., "Identification and Behavior of Label–retaining Cells in Oral Mucosa and Skin", *J. Dent. Res., 122C,* (Aug. 1981),1611–1620.
Bickenbach, J. R., et al., "Identification and Locatlization of Label–Retaining Cells in Hamster Epithelia", *J. Invest. Dermatol., 82:6,* (Jun. 1984),618–622.
Bickenbach, J. R., et al., "Label–Retaining Cells in Human Embryonic and Fetal Epidermis", *J. Invest. Dermatol. 88,* (Jan. 1987),42–46.
Bickenbach, J. R., et al., "Rate of loss of tritiated thymidine label in basal cells in mouse epithelial tissues", *Cell Tissue Kinet, 19,* (May 1986),325–333.
Bickenbach, J. R., et al., "Selection and Extended Growth of Murine Epidermal Stem Cells in Culture", *Experimental Cell Research 244,* (1998),184–195.
Bickenbach, J. R., et al., "Transduction of a Preselected Population of Human Epidermal Stem Cells: Consequences for Gene Therapy", *Proceedings of the ASsociation of American Physicians, III:3,* XP–002182787,(May/Jun. 1999),184–189.
Blau, H. , et al., "Gene therapy: Progress, problems, prospects", *Nature Medicine, 3:6,* (Jun. 1997),612–613.
Chung, S. Y., "Expression of the Human Keratin Gene (K1) in Transgenic Mice is Tissue– and Development–Specific but Altered with Respect to Differentiation State", *Molecular and Cellular Differentiation, 2(1),* (1994),61–81.
Compton, C. C., et al., "Skin Regenerated from Cultured Epithelial Autografts on Full–Thickness Burn Wounds from 6 Days to 5 Years after Grafting", *Laboratory Investigation, 60(5),* (May 1989),600–612.
Dellambra, E. , et al., "Corrective Transduction of Human Epidermal Stem Cells in Laminin–5–Dependent Junctional Epidermolysis Bullosa", *Human Gene Therapy, 9,* (1998), 1359–1370.
Deng, H. , et al., "Sustainable cutaneous gene delivery", *Nature Biotech, 15(13),* (Dec. 1997),1388–1391.

(Continued)

*Primary Examiner*—Leon B. Lankford, Jr.
(74) *Attorney, Agent, or Firm*—Schwegman, Lunberg, Woessner & Kluth, P.A.

(57) ABSTRACT

A method to prepare epidermal stem cells, and isolated epidermal stem cells, is provided. Also provided are methods of using epidermal stem cells, e.g., for cell based therapies.

29 Claims, 8 Drawing Sheets

OTHER PUBLICATIONS

Fenjives, E. S., et al., "Loss of Expression of a Retrovirus–Transduced Gene in Human Keratinocytes", *J. Invest. Dermatol.*, 106(3), (Mar. 1996),576–578.

Fibison, W. J., "Gene Therapy", *Nursing Clinics of North America*, 35(3), (Sep. 2000),757–772.

Flowers, M. E., et al., "Long–term transplantation of canine keratinocytes made resistant to G418 through retrovirus–mediated gene transfer", *Proc. Natl. Ada. Sci. USA*, 87(6), (Mar. 1990),2349–2353.

Fuchs, E. , "Epidermal Differentiation: The Bare Essentials", *J. Cell Biol.*, 111(6), (Dec. 1990),2807–2814.

Garlick, J. A., et al., "Keratinocyte Gene Transfer and Gene Therapy", *Crit Rev Oral Biol Med*, 7(3), (1996),204–221.

Garlick, J. A., et al., "Retrovirus–Mediated Transduction of Cultured Epidermal Keratinocytes", *J. Investe. Dermatol.*, 97(5), (Nov. 1991),824–829.

Ghazizadeh, S. , et al., "In vivo transduction of mouse epidermis with recombinant retroviral vectors: implications for cutaneous gene therapy", *Gene Therapy*, 6(7), (Jul. 1999),1267–1275.

Goodell, M. A., et al., "Isolation and Functional Properties of Murine Hematopoietic Stem Cells that are Replicatiang in Vivo", *J. Exp. Med.*, 183(4), (Apr. 1996),1797–1806.

Greenhalgh, D. , et al., "Epidermis: An Attractive Target Tissue for Gene Therapy", *J. Invest. Dermat.*, 103(5), (Nov. 1994,63S–69S.

Jackson, K. A., et al., "Hematopoietic potential of stem cells isolated from murine skeletal muscle", *Proc. Natl. Acad. Sci. 96(25)*, (Dec. 1999),14482–14486.

Khavari, P. A., "Therapeutic gene delivery to the skin", *Molecular Medicine Today*, 3, (1997),533–538.

Korge, B. P., et al., "The molecular basis for inherited bullous diseases", *J. Biol. Med.*, 74(2), (Feb. 1996),59–70.

Mackenzie, I. , et al., "Influence of Connective Tissues on the In Vitro Growth and Differentiation of Murine Epidermis", *Epith. Cell Biol.*, 2(3), (1993),107–119.

Mackenzie, I. , "Retroviral Transduction of Murine Epiermal Stem Cells Demonstrates Clonal Units of Epidermal Structure", *J. Invest. Dermatol.*, 109(3), (Sep. 1997),377–383.

Morgan, J. R., et al., "Expression of an Exogenous Growth Hormone Gene by Transplantable Human Epidermal Cells", *Science*, 237, (Sep. 1987),1476–1479.

Morris, R. J., et al., "Highly Persistent Label–Retaining Cells in the Hair Follicles of Mice and Their Fate Following Induction of Anagen", *J. Invest. Dermatol.*, 112(4), (Apr. 1999),470–475.

Mountain, A. , "Gene therapy: the first decade", *Trends in Biotechnology*, 18(3), (Mar. 2000),119–128.

Otto, W. R., et al., "Survival of Allogeneic Cells in Cultured Organotypic Skin Grafts", *Plast. Reconstr. Surg.*, 96(1), (Jul. 1995), 166–176.

Reddi, A. H., "Morphogenesis and tissue engineering of bone and cartilage: inductive signals, stem cells, and biomimetic biomaterials", *Tissue Engineering*, 6(4), (2000), 351–359.

Rheinwald, J. G., et al., "Serial cultivation of strains of human epidermal keratinocytes: the formation of keratinizing colonies of single cells", *Cell*, 6(3), (Nov. 1975),331–344.

Rothnagel, J. A., et al., "Analysis, diagnosis, and molecular genetics of keratin disorders", *Current Opinion in Dermatology*, (1995),211–218.

Sanes, J. R., "Analysing cell lineage with a recombinant retrovirus", *Trends in Neurosciences*, 12(1), (1989),21–28.

Stenn, K. S., et al., "Dispase, a neutral protease from *Bacillus Polymyxa*, is a powerful fibronectinase and Type IV collagenase", *J. Inveset. Dermat.*,93(2), (Aug. 1989),287–290.

Vogel, J. C., "Keratinocyte Gene Therapy", *Arch. Dermat.*, 129, (Nov. 1993),1478–1483.

Vogt, P. M., et al., "Genetically modified keratinocytes transplanted to wounds reconstitute the epiermis", *Proc. Natl. Acad. Sci.*, 91(20), (Sep. 1994),9307–9311.

Walther, W. , et al., "Therapeutic genes for cancer gene therapy", *Molecular Biology*, 13(1), (Nov. 1999),21–28.

Wang, F. , et al., "Gene therapy and metabolic engineering", *Metabolic Engineering*, 2, (2000),126–139.

* cited by examiner

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: A primer

<400> SEQUENCE: 1
aagttcatct gcaccaccg                                                  19

<210> SEQ ID NO 2
<211> LENGTH: 20
<212> TYPE: DNA
<213> ORGANISM: Artificial Sequence
<220> FEATURE:
<223> OTHER INFORMATION: A primer

<400> SEQUENCE: 2
tgctcaggta gtggttgtcg                                                 20

<210> SEQ ID NO 3
<211> LENGTH: 20
<212> TYPE: DNA
<213> ORGANISM: Artificial Sequence
<220> FEATURE:
<223> OTHER INFORMATION: A primer

<400> SEQUENCE: 3
cgaccacatg aagcagcacg                                                 20

<210> SEQ ID NO 4
<211> LENGTH: 20
<212> TYPE: DNA
<213> ORGANISM: Artificial Sequence
<220> FEATURE:
<223> OTHER INFORMATION: A primer
```

-continued

<400> SEQUENCE: 4
gttctgctgg tagtggtcgg                    20

METHODS TO PREPARE AND USE EPIDERMAL STEM CELLS

CROSS REFERENCE TO RELATED APPLICATIONS

This application claims priority under 35 U.S.C. §119(e) from U.S. provisional application Ser. No. 60/192,754, filed Mar. 28, 2000.

STATEMENT OF GOVERNMENT RIGHTS

The invention was made, at least in part, with a grant from the Government of the United States (grants RO1-AR45259 and P60-DK54759 from the National Institutes of Health). The Government may have certain rights to the invention.

BACKGROUND OF THE INVENTION

One of the main problems with designing a gene therapy approach for a continuously renewing tissue, such as the epidermis of the skin, is that most of the cells transfected or transduced with the target genes are eventually sloughed into the environment (Morgan, 1987; Vogt, 1994; Huber, 1995; Choate, 1996; Fenjives, 1996; Freiberg, 1997; Dellambra, 1998; Seitz, 1999). Epidermal tissue integrity is maintained by division of cells in the proliferative basal layer to replace differentiated cells in the outermost stratum corneum layer that are continually lost. In human and mouse epidermis, most of the cells are replaced every twenty days (Gelfant, 1982). This hierarchy of cell proliferation and differentiation is maintained by a small subpopulation of stem cells (for a review see Potten, 1997), which slowly proliferate. It has been known for decades that epithelial stem cells can be identified as label-retaining cells (LRCs) by long term retention of a nuclear label. It has been assumed that epidermal stem cells are a self-renewing population in which, on average, each cell division produces one stem cell and one transient amplifying (TA) cell. The TA cells, as their name implies, amplify the basal cell population, but they are limited to a finite number of cell divisions before their progeny must commit to differentiate and are ultimately sloughed into the environment. Only the stem cells remain and continue to proliferate for the lifetime of the epidermis (Cairns, 1975). This implies that any genetic treatment must be directed toward the stem cell genome. Unfortunately, isolating a pure population of epidermal stem cells has been problematic.

The main function of the skin is to provide a protective barrier for the internal tissues of the body. When this barrier is broken, it can be life-threatening as the body loses fluids and is exposed to harmful factors in the environment. Allogeneic grafts made from cultured epidermal cells that had been expanded at least ten-fold have been shown to last for years (Rheinwald, 1975; Otto, 1993; Compton, 1989. Although these grafts do not usually form all of the epidermal appendages, such as hair follicles and sweat glands, they reform a structured epidermis with spinous, granular, and cornified cells overlying the basal cell compartment, suggesting that epidermal stem cells survived and replicated during the culturing procedure.

The next steps are to use epidermal stem cells to bioengineer a complete skin and to use epidermal stem cells to deliver genes for permanent gene therapy. For delivery of genes to a variety of cell types, replication deficient viral vectors have been the major vehicles (Garlick, 1991; Vogt, 1994; Ng, 1997). Using a retroviral-LacZ gene for transduction into the epidermis, several investigators reported good initial expression in keratinocytes, but disappearance within 14 to 40 days (Morgan, 1987; Vogt, 1994; Fenjives, 1996). Loss of expression was thought to be due to selective methylation of viral promoters (Fenjives, 1996) or to the loss of the transduced cells (Kolodka, 1998). In support of the latter view, recent studies have reported migration of transduced cells through the differentiated layers of the epidermis, with only a few keratinocytes showing long term expression (Flowers, 1990; Mackenzie, 1997; Deng, 1997; Ghazizadeh, 1999). Thus, it seems likely that total loss of expression in a tissue may be due to the failure to transduce stem cells. This might happen because stem cells make up a very small percentage of the basal cell population. Thus, any method that increases the percentage of stem cells in the population should increase the possibility of transfecting stem cells, thereby improving gene therapy approaches.

Thus, what is needed is a method to prepare a population of substantially pure epidermal stem cells, which cells are useful to form tissues or to deliver genes.

SUMMARY OF THE INVENTION

The invention provides a method to prepare isolated mammalian epidermal stem cells, which are undifferentiated self-renewing cells. The method comprises separating a population of mammalian epidermal cells comprising epidermal stem cells into a substantially pure population of epidermal stem cells and, preferably, at least one population of cells that does not comprise a substantial portion, e.g., less than a detectable amount, of epidermal stem cells. As used herein, a "substantially pure population of epidermal stem cells" means that the population has less than about 20%, preferably less than about 10%, more preferably less than about 8%, even more preferably less than about 5%, and yet even more preferably less than about 1%, e.g., less than a detectable amount as determined by methods known to the art, of cells which are not stem cells, for example TA cells. That is, the method of the invention provides a population of epidermal stem cells that is at least 80%, preferably 90%, more preferably at least 92%, even more preferably at least 95% and yet even more preferably at least 99%, pure. Then the epidermal stem cells are isolated. The cells may be primate cells, e.g., human cells, or non-primate cells, e.g., bovine, equine, porcine, feline, canine, ovine, or murine cells. Sources for the mammalian epidermal cells include, but are not limited to, epidermal tissue from an adult, a neonate or fetus. The tissue is preferably dissociated by separating the epidermis from the dermis. In one embodiment of the invention, the population of mammalian epidermal cells is contacted with an agent that binds DNA in viable cells, e.g., a dye such as a Hoechst dye and more preferably a Hoechst dye having low or no toxicity, prior to separation. In another embodiment, the population of mammalian epidermal cells is contacted first with an agent that binds DNA in viable cells, and then with an agent that binds to non-viable cells, e.g., propidium iodide or pyronidine iodine, prior to separation. Preferably, the media employed prior to, during, and subsequent to the separation does not comprise an agent that decreases the viability of keratinocytes, e.g., keratinocytes are sensitive to azide. In a further embodiment, the population epidermal cells is separated by size, either before, during or after selection based on dye profile. As described hereinbelow, it was found that epidermal stems cells are found in the highest concentration in the smallest cells of a sample of mammalian epidermal cells, i.e., cells which represent the smallest 5 to 35%, and preferably smallest 14 to 32%, for example, smallest 25%, of cells in the sample. The method of the invention thus provides a substantially pure population of epidermal stem cells which can be expanded to large numbers. The invention further provides isolated epidermal stem cells.

As described hereinbelow, using a Hoechst and propidium iodide dye combination and specifically-defined gating, mouse epidermal basal cells were sorted into three distinct subpopulations: stem, transient amplifying (TA), and non-proliferative basal cells. More than 90% of freshly isolated stem cells showed a G0/G1 cell cycle profile, while greater than 20% of the TA cells were actively dividing. Both stem and TA cells retained proliferative capacity, but the stem cells formed larger, more expandable colonies in culture. Both populations could be transduced with a retroviral vector and used to bioengineer an epidermis. However, only the epidermis from the stem cell population continued to grow and express the reporter gene for six months in organotypic culture. The epidermis from the transient amplifying cell fraction completely differentiated by two months. Thus, this method yields a pure population of keratinocytes that shows all of the functional characteristics of stem cells, including high proliferative capacity, tissue regeneration, and long term expression of a transduced reporter gene. These epithelial stem cells are useful to bioengineer a tissue and for gene therapy.

Using the above-described method including sorting cells based on size, neonate back skin and adult ear and footpad were separated into stem cells and TA cells. There were twice as many stem cells in neonate back skin compared to adult ear and adult footpad (8.4% vs. 3.7 and 3.8%). All the stem cells exhibited a similar cell cycle profile with about 96% in G0/G1 and only 4% dividing. Neonate back skin and adult footpad TA cells exhibited a more typical neonate epidermal profile of 85% in G1 and 15% dividing. However, adult ear TA cells showed a more stem-cell like cell cycle profile. To confirm that cells are cycling, a BrdU pulse as well as cyclin B1 staining was performed. Positive cells were found in each group, indicating that stem cells were cycling. Taking together, these data show quantitatively that the cell cycle profile of adult TA cells is dependent of the proliferative state of the tissue they maintain, whereas the cell cycle profile of stem cells is their intrinsic property.

As also described hereinbelow, epidermal stem cells marked with GFP were injected into lethally-irradiated mice and the location of GFP+ cells determined. The results indicated that epidermal stem cells likely can differentiate into mesenchymally-derived tissues such as adipose and hematopoietic cells and may have the capacity to replenish hematopoietic cell lineages. Further evidence of the pluripotent native of epidermal stem cells was shown when GFP-marked epidermal stem cells were injected into murine blastocysts. The resulting chimeras were placed in pseudopregnant female mice and the progeny characterized. The GFP-marked epidermal stem cells were found in liver, cartilage and connective tissue, as well as placenta.

Thus, the invention provides a method to prepare isolated mammalian epidermal stem cells which comprises separating in a sample comprising a population of mammalian epidermal cells, a population comprising epidermal stem cells from at least one population of cells that does not comprise epidermal stem cells. Then a substantially pure population of epidermal stem cells is isolated from the population of epidermal stem cells. For example, epidermal stem cells may be separated from other cells using agents which have differential binding properties for stem cells versus non-stem cells and/or by size. The epidermal stem cells may then be isolated based on a different property of those cells, e.g., if the separation employs an agent with differential binding properties, the isolation may be accomplished by size separation.

Also provided is a method to prepare isolated mammalian epidermal stem cells which comprises separating in a sample comprising a population of mammalian epidermal cells, a population in the sample which represents the smallest 30% of the cells in the sample and which population comprises epidermal stem cells, from larger cells in the sample. A substantially pure population of epidermal stem cells is then isolated from the smaller cells. Preferably, the substantially pure population of epidermal stem cells is isolated based on the dye binding properites of epidermal stem cells.

Further provided is a method to prepare isolated mammalian epidermal stem cells, comprising: (a) contacting a population of mammalian epidermal cells comprising epidermal stem cells with an amount of a first agent under conditions effective for viable cells to retain the first agent; (b) contacting the population of (a) with an amount of a second agent under conditions effective for non-viable cells to retain the second agent; and (c) separating the population of (b) into a population of viable epidermal stem cells and at least one population of cells that does not comprise epidermal stem cells. For a first agent that is a Hoechst dye such a Hoechst 33342, a preferred concentration is about 1 $\mu$g/ml to about 10 $\mu$g/ml, and more preferably about 2 $\mu$g/ml to about 5 $\mu$g/ml, of the agent. Preferred concentrations of a second agent such as propidium iodide include a concentration of about 0.05 $\mu$g/ml to about 10 $\mu$g/ml, and more preferably about 1 $\mu$g/ml to about 5 $\mu$g/ml, of the second agent.

The isolated epidermal stem cells of the invention are useful to bioengineer a tissue and/or for gene therapy or cell therapy. Hence, the invention provides a method of using isolated epidermal stem cells. The method comprises contacting the isolated stem cells with an isolated nucleic acid molecule so as to yield transformed epidermal stem cells. Then transformed epidermal stem cells are identified. For example, the cells may be contacted with recombinant DNA encoding a therapeutic gene product or a recombinant DNA comprising a marker or selectable gene. In one embodiment, the recombinant nucleic acid molecule can be delivered by a recombinant virus, e.g., a recombinant retrovirus, lentivirus, herpes virus, adenovirus, or adeno-associated virus.

The isolated epidermal stem cells of the invention, e.g., transformed or non-transformed cells, may be employed to prepare a tissue in vitro. The tissue may be skin, e.g., for grafting or a patch useful to deliver a gene product, oral mucosa or a blood vessel. In particular, given the low immunogenicity of keratinocytes, the cells of the invention and their progeny are particularly useful for bioengineering of tissues and for gene therapy.

Figure 5:
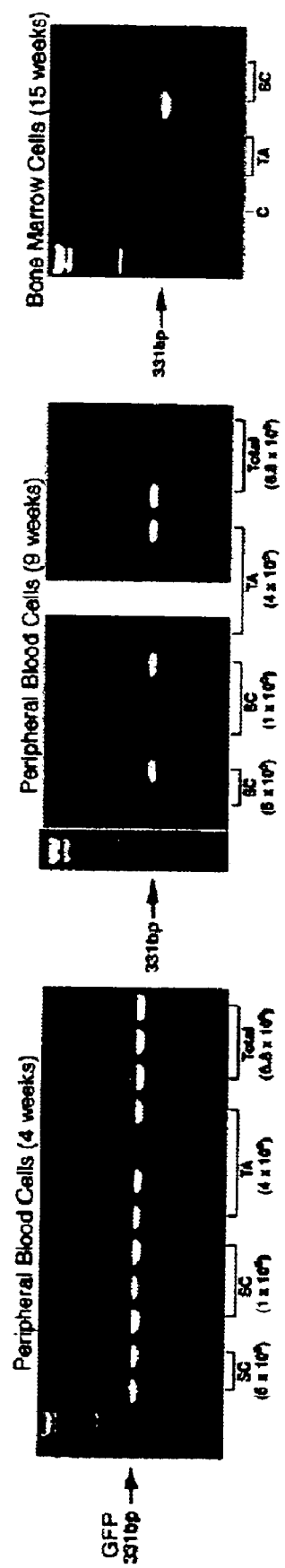

FIG. 5. PCR analysis of genomic DNA from blood drawn 4–9 weeks, or from bone marrow at 15 weeks, after injection of stem cells ( SC), TA cells or total basal cells into lethally-irradiated mice. At 4 weeks, the surviving mice showed the presence of the GFP gene in all but one TA specimen. At 9 weeks after injection, all groups showed a decrease in the number of GFP+ cells (2 SC or total, 1 TA). At 15 weeks, only one mouse ( SC) showed the presence of GFP+ cells. The results suggest that epidermal stem cells are surviving in either the bone marrow or circulating blood.

Figure 6:
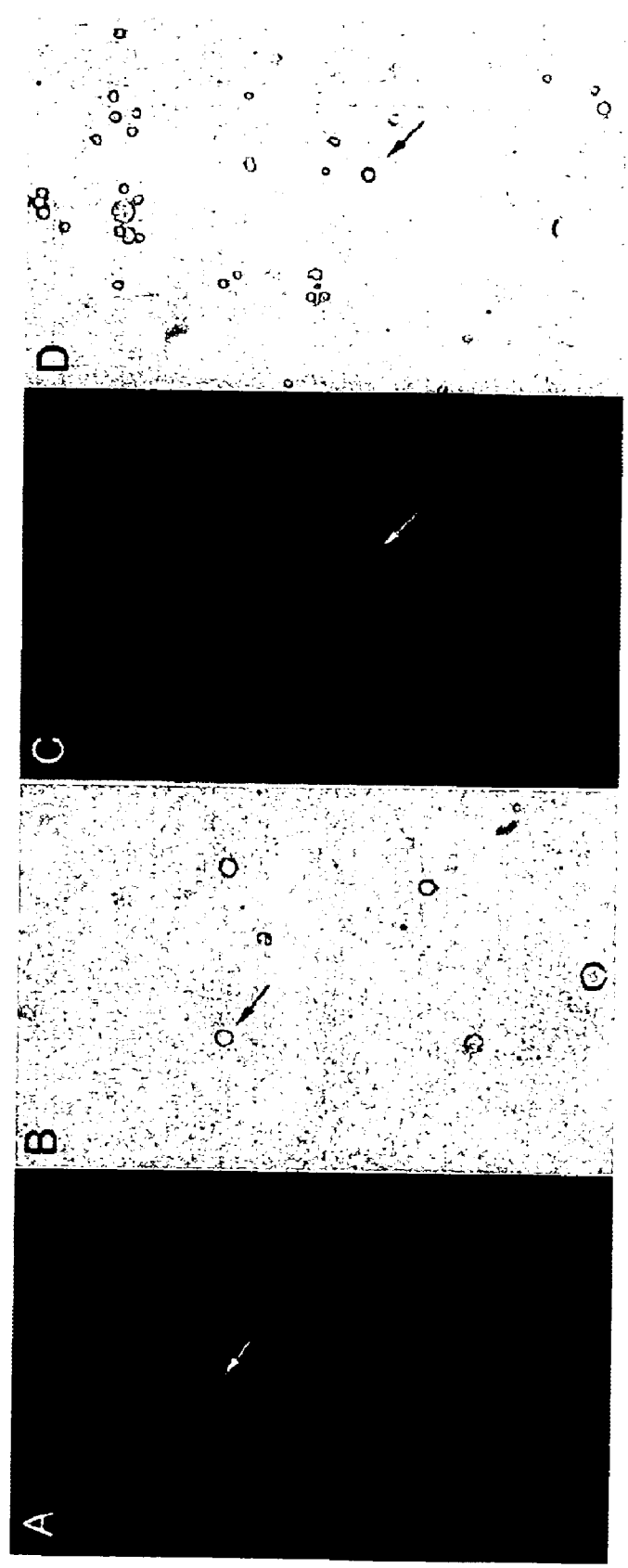

FIG. 6. Immunofluorence of bone marrow cells harvested 15 weeks after injection of SC or TA cells. A few GFP+ cells (about 1/10,000) were observed in a mouse that received SC cells, while no GFP+ cells ($<1 \times 10^7$ cells) were observed in 2 mice that received TA cells.

Figure 7:
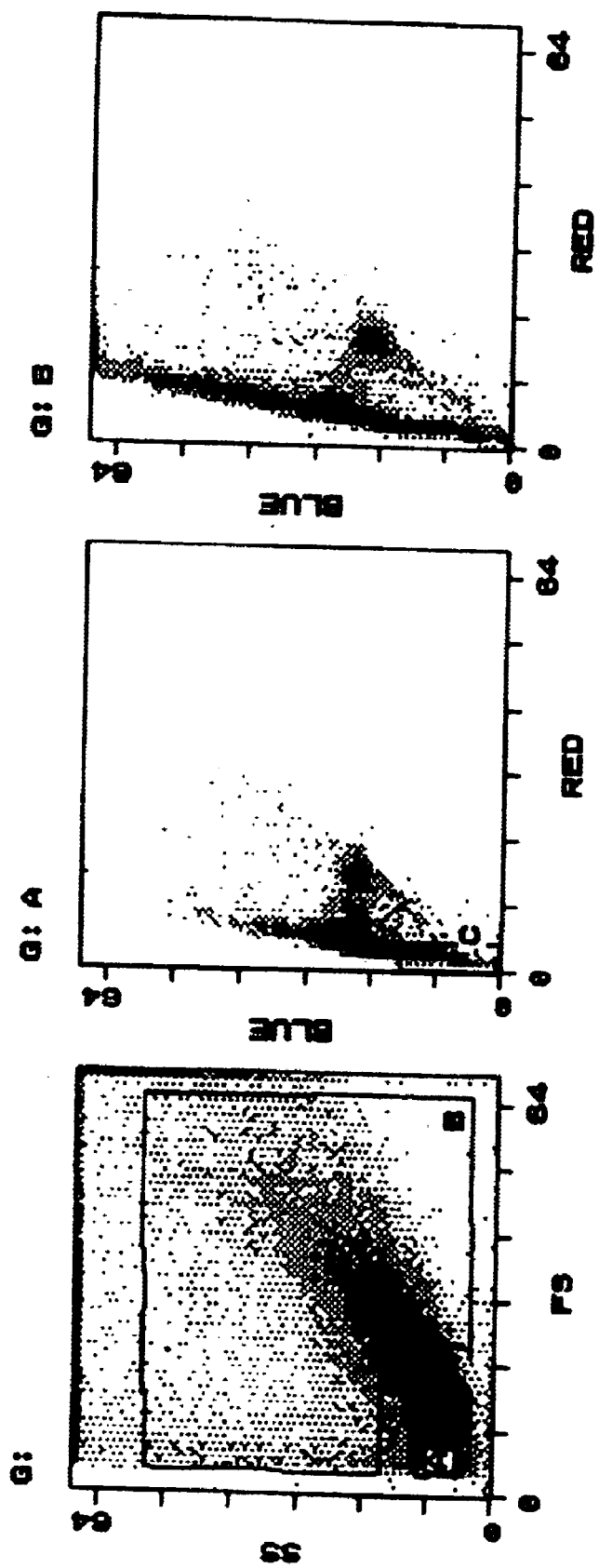

FIG. 7. Basal cells from mouse skin were sorted into stem and TA populations first based on size, then based on Hoechst red/blue dye exclusion. A) This graph shows the size distribution of mouse basal keratinocytes. B) and C) show the Hoechst red and blue staining characteristics of the cells from box A (panel B) and box B (panel C) from panel A. The cells in box A represent the smallest 25% of the basal cells. Epidermal stem cells were the small cells in box A with low Hoechst red/blue staining and represent 3–4% of total basal popluation in adult and 6–8% in neonate(box C in panel B). TA cells are in box B in panel A and represent about 30% of the total basal population. All cells in C and B express K14 but not K1.

Figure 8:
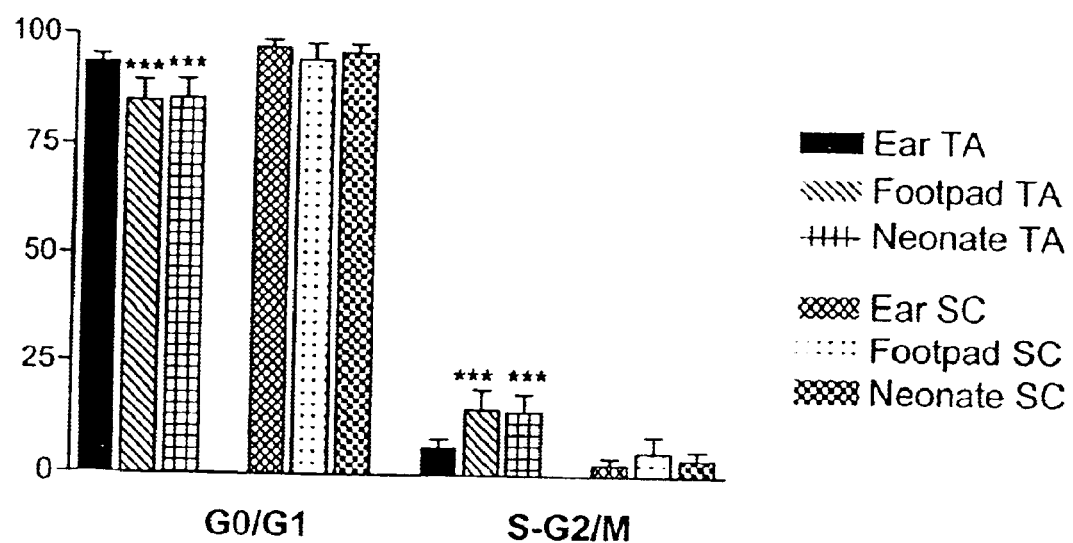

FIG. 8. Percent of stem cells and TA cells in G0/G1 or S-G2/M in cells isolated from adult and neomnate mice. *** $p<0.001$ after a one-way non parametric ANOVA and Newman-Keuls as post hoc test.

DETAILED DESCRIPTION OF THE INVENTION

The invention provides methods to isolate and use epidermal stem cells. The isolated epidermal cells have an expanded proliferative capacity relative to non-stem cells and may be induced to differentiate into ectoderm-derived tissues or mesoderm-derived tissues. Methods to induce cells to differentiate into a particular cell type are known to the art. Given the large proliferative capacity of the epidermal stem cells, large numbers of these cells can be prepared, e.g., to prepare tissue for grafting, and, optionally, transformed with recombinant nucleic acid, e.g., to deliver therapeutic gene products such as factor VIII, factor IX, growth hormone, transferrin, epidermal growth factor, cytokines such as TNF, interleukins (interleukins 1–12), interferons ($\alpha$, $\beta$, $\lambda$, -interferons), adenosine deaminase, low-density lipoprotein receptor, $\beta$-glucuroniclase, type VIII collagen, keratins 1–21, fumaryl-acetoacetate hydrolase, cystic fibrosis transductance membrane regulator CFTR, lecithin, transforming growth factor beta, cholesterol acyltransferase, FAS ligand, nitric oxide synthase, erythropoietin and the like. Moreover, the cells of the invention are preferred sources for bioengineering tissue and/or gene therapy as these cells have low immunogenicity. For example, epidermal stem cells transduced with VEGF may be introduced to diabetic mammals to inhibit or treat ischemia.

The invention will be further described by the following non-limiting examples.

EXAMPLE 1

Materials and Methods
Preparation of Cells for Flow Cytometry

Label-retaining cells were made as previously described (Bickenbach, 1998). Briefly, ten and eleven day old mice were given four injections of BrdU, then allowed to grow for 30 days with no further labeling. At then end of the chase period, the adult mouse ears were incubated in 3 mM EDTA at 37° C. and the epidermis separated from the dermis; the epidermal sheets were placed for 10 minutes in a sterile tube containing 0.25% trypsin at 37° C. and gently shaken to dissociate into single cells. The dissociated basal cells were centrifuged and resuspended at $10^7$ cells/ml in SMEM (Life Technologies, Grand Island, N.Y., USA) with 0.05 mM $Ca^{++}$, 2% chelexed FBS, 1 mM Hepes, 1% penicillin-streptomycin, and 2.5 µg/ml Hoechst 33342. Cells were incubated at 37° C. for 90 minutes, centrifuged, and resuspended in 1 µg/ml propidium iodide in SMEM and kept on ice until the flow cytometric procedure. Neonate epidermal cells were prepared as previously described (Bickenbach, 1998). Briefly, backskin was incubated in cold trypsin overnight, the epidermis removed from the dermis, and the basal cells dissociated by gentle shaking the epidermis in medium. For sorting, these cells were stained as described above.

Flow Cytometry

Cell sorting was performed on a Coulter EPICS 753. Forward and orthogonal scatter signals were generated using 100 mW at 488 nm. Hoechst 33342 and propidium iodide were excited with 100 mW of UV (351–364 nm). Hoechst fluorescence was measured through a 440/60 nm bandpass filter while propidium iodide was measured through a 670/14 nm bandpass filter. All parameters were collected using linear amplification in listmode. To reduce shear forces during sorting, sheath pressure was reduced from 13 to 9 PSI which required the drop drive frequency to be reduced from 32 to 19 kHz. SMEM was used in place of PBS for the sheath fluid to aid in keeping the cells alive. Stem cells (fraction 1) were sorted using gates placed around the population exhibiting low to medium forward and orthogonal scatter, and low Hoechst and propidium iodide fluorescence. Transient amplifying cells (fraction 2) were collected on the basis of high forward and orthogonal scatter, and low propidium iodide fluorescence, but no regard for Hoechst fluorescence. In separate runs the cells not collected in fractions 1 and 2 were collected as fraction 3. After sorting, cells were processed for antibody staining, or cultured for growth studies or for transfection.

Antibody Staining

Sorted populations of stem and TA cells were spread onto slides, air-dried, fixed in ethanol at –20° C., then stained for BrdU and keratin K14 as previously described (Bickenbach, 1998). Briefly, cells were rinsed in PBS, then incubated overnight with mouse monoclonal anti-BrdU (FITC-conjugated, Becton Dickinson, Bedford, Mass., USA) and affinity purified guinea pig anti-keratin K14 (a generous gift from D. Roop), rinsed and incubated with biotinylated goat anti-guinea pig (Vector, Burlingame, Calif., USA), and with streptavidin Texas Red (Life Technologies, Grand Island, N.Y., USA). The number of LRCs (BrdU+ cells) and the total number of basal cells (K14+ cells) were counted in each sorted population and the percentage of LRCs and standard deviations calculated. To determine whether cells had entered the differentiation pathway, some cells from each group were stained with rabbit anti- K1 (a generous gift from D. Roop) and the percentage of K1+ cells determined.

Cell Cycle Profile Analysis

Cell cycle profiles of sorted neonate mouse stem and TA cells, and total neonate and adult basal cells were determined as described by Nicoletti (1991). Keratinocytes were centrifuged and resuspended at $1\times10^6$ cells/ml in a hypotonic propidium iodide solution (1mM Tris, 0.1 mM EDTA, 0.1% Triton-X100, 3.4 mM Na Citrate, 0.05 mg propidium iodide). The cells were allowed to sit in the stain on ice for at least 15 minutes before processing through the FACScan (Becton-Dickenson) flow cytometer. DNA content was measured using an excitation wavelength of 488 nm and an emission wavelength of 4585 nm, and analyzed using the CellQuest® v3.2 software program (Becton-Dickenson). The data were graphed with ModFit LT v2.0 software (Verity Software House, Inc.).

Cell Culture and Tissue Engineering

Neonate mouse sorted stem, TA, and basal cells were cultured using a method and medium designed for long-term culture of mouse keratinocytes (Bickenbach, 1998). Briefly, sorted cells were grown on collagen type IV coated dishes (Collaborative Biomedical, Bedford, Mass., USA) in low calcium SMEM medium+9% chelexed FBS, 1% antibiotic/antimycotic (Life Technologies) at a concentration of $5\times10^5$ cells per 35 mm dish. The low amount of calcium and the additional growth factor present in this formulation maintained both the freshly isolated and sorted stem and transient amplifying mouse cells and allowed them to grow in submerged culture. Each culture was subcultured at 90% confluence and $5\times10^5$ cells plated per 35 mm dish. The number of population doublings for each population was determined.

To test whether sorted epidermal stem and transient amplifying cells had the capacity to reform a complete epithelium, colonies formed from either the sorted stem population or the transient amplifying population were cultured for one week, then removed from the culture dish by incubation at 37° C. in dispase II (Roche Molecular Biochemicals, Indianapolis, Ind., USA). The still intact colonies were gently placed on top of a bioengineered dermis (see below), making sure to keep the correct orientation. The colonies were allowed to attach for four days in submerged culture in a 37° C. $CO_2$ incubator, then the bioengineered tissue was raised to the air-liquid interface by placing onto a stainless steel mesh rack in a 35 mm culture dish, and medium added so that the cultures were fed from below. Samples were taken after 2 and 6 months in organotypic culture.

The bioengineered dermis was made by mixing 1.2 mg/ml of rat tail collagen type I (Collaborative Biomedical, Bedford, Mass., USA) with DMEM, 20% FBS, 50 µg/ml ascorbic acid, 0.3% 1N NaOH, and $1\times10^5$ mouse skin fibroblasts. The fibroblasts were isolated from neonate mouse backskin by incubating the skin in cold trypsin overnight, separating the dermis from the epidermis, and digesting the dermis in 0.2% collagenase at 37° C. for 1 hour. The cells were grown in DMEM+ 10% FBS+50 µg/ml ascorbic acid for 1–2 passages before using them to bioengineer a dermal substitute. The fibroblasts were allowed to contract and remodel the collagen gel for two weeks at 37° C. before colonies made from the sorted keratinocytes were added.

Transduction and x-gal Staining

Stem and TA cells were isolated as described above, plated on collagen type IV coated dishes, and allowed to grow for 48–72 hours. The adherent cells were transfected with a replication defective retroviral vector with amphotropic envelopes and carrying a Lac Z reporter gene (retro.LacZ) (supplied by The University of Iowa Vector Core using the Cosset packing cell line for the amphotropic MuLV, TA7) (Cosset, 1995; Kitten, 1997). For transfection, 1.5 ml of medium with $5\times10^7$ retro.LacZ particles and 15 µg of polybrene (Sigma) was added to the dishes and incubated at 37° C. for 3 hours, then 1.5 ml of medium added and the dishes incubated overnight. After two days the dishes were fed with N-medium (Hager, 1999) and the next day the cells were subcultured. At confluence, cultures to be stained with X-gal were fixed in buffered mixture of paraformaldehyde (2%) and glutaraldehyde (0.2%) for 10 minutes at 4° C., then incubated overnight at 37° C. in a 3 mg/ml solution of buffered x-gal (5-bromo-4-chloro-3-indoyl B-D-galactopyranoside) (pH 8.6). The number of gal expressing cells (blue-stained) and non- gal expressing cells were determined, and the transfection percentage calculated. Bioengineered tissues to be stained with x-gal were treated the same as the cultures, except they were fixed for 1 hour. After x-gal staining, the tissues were secondarily fixed in half-strength Karnovsky's fixative (Karnovsky, 1965; embedded in EMbed 812 (Electron Microscopy Sciences, Fort Washington, Pa., USA)), and 1 µsections stained with Richardson's stain (Hayat, 1972), then examined for reformation of a stratified epidermal structure and gal expression.

Results

Mouse Ear Epidermis Contains Three Distinct Populations of Basal Cells

Figure 1:
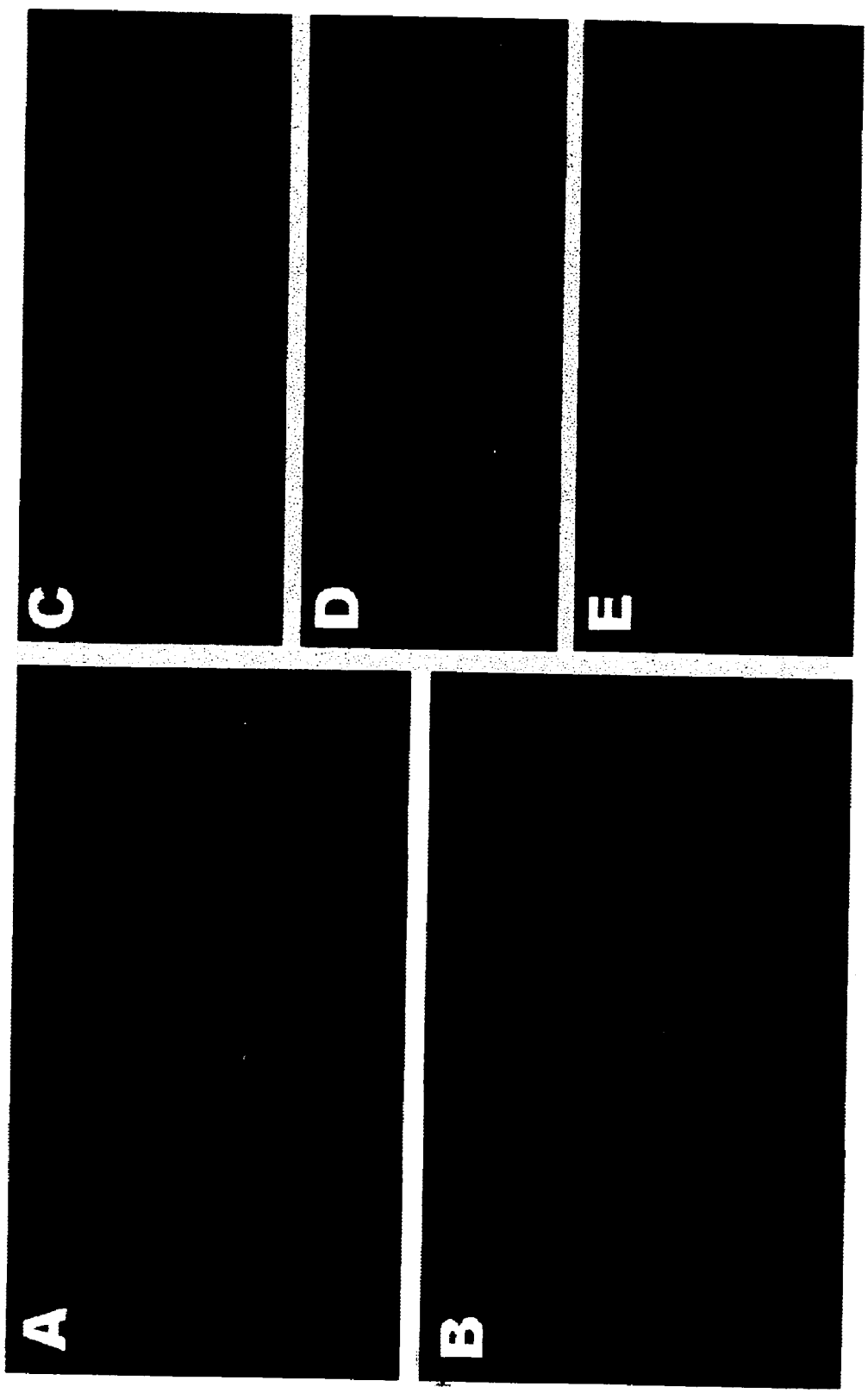
FIG. 1. Immunofluorescence of sorted mouse epidermal basal cells. Cells were stained with antibodies to keratin K14 (Texas Red) and/or antibodies to BrdU (FITC). A & B) stem fraction (Red stain=K14 only, Yellow stain=K14 and BrdU), C) TA fraction (K14 only), D) TA fraction (BrdU only). E) other basal cell fraction (K14).

Previously, it has been shown that keratinocytes with stem cell characteristics retain a nuclear label, such as $^3$H-thymidine or bromodeoxyuridine (BrdU), for several months after labeling (Bickenbach, 1981; Bickenbach, 1986; Bickenbach, 1998). In this study, freshly isolated mouse ear epidermal cells from BrdU-label-retaining mice were prepared using a sorting technique (Goodell, 1996) that was modified for keratinocytes. Based upon dye characteristics, it was found that adult mouse epidermal basal cells could be sorted into three distinct populations (FIG. 1, Table 1), referred to as stem, transient amplifying (TA), and other basal cells. All three populations were identified as basal by their expression of K14, a keratin marker of basal cells (Fuchs, 1990), and their lack of K1 expression, a keratin upregulated when basal cells leave the proliferative pool and commit to differentiate into spinous cells (Chung, 1994). Fraction 1 (stem) represented about 3.5% of the basal cell population, and 95% of these cells were LRCs. Fraction 2 (TA) contained nearly 90% of the basal cells and virtually no LRCs. Fraction 3 (other basal) represented about 8% of the basal cells. Even though the cells in fractions 2 and 3 were both K14+/ BrdU−, the two populations could be differentiated because the cells in fraction 3 did not plate or grow in culture, suggesting that although these cells still expressed the basal cell marker K14 and did not express the differentiation marker K1, they had already left the proliferative pool and begun to differentiate. Using the same parameters, neonate mouse epidermal basal cells were sorted into three distinct populations, which were used for cell cycle and culture experiments.

TABLE 1

| Cell Type[+] | % of Total[^] | % of LRCs[^,*] |
|---|---|---|
| Stem | 3.4 ± 0.2 | 95.3 ± 2.1 |
| Transient Amplifying | 89.2 ± 1.1 | 0.1 ± 0.1 |
| Other Basal | 7.4 ± 0.9 | 0 |

Figure 2:
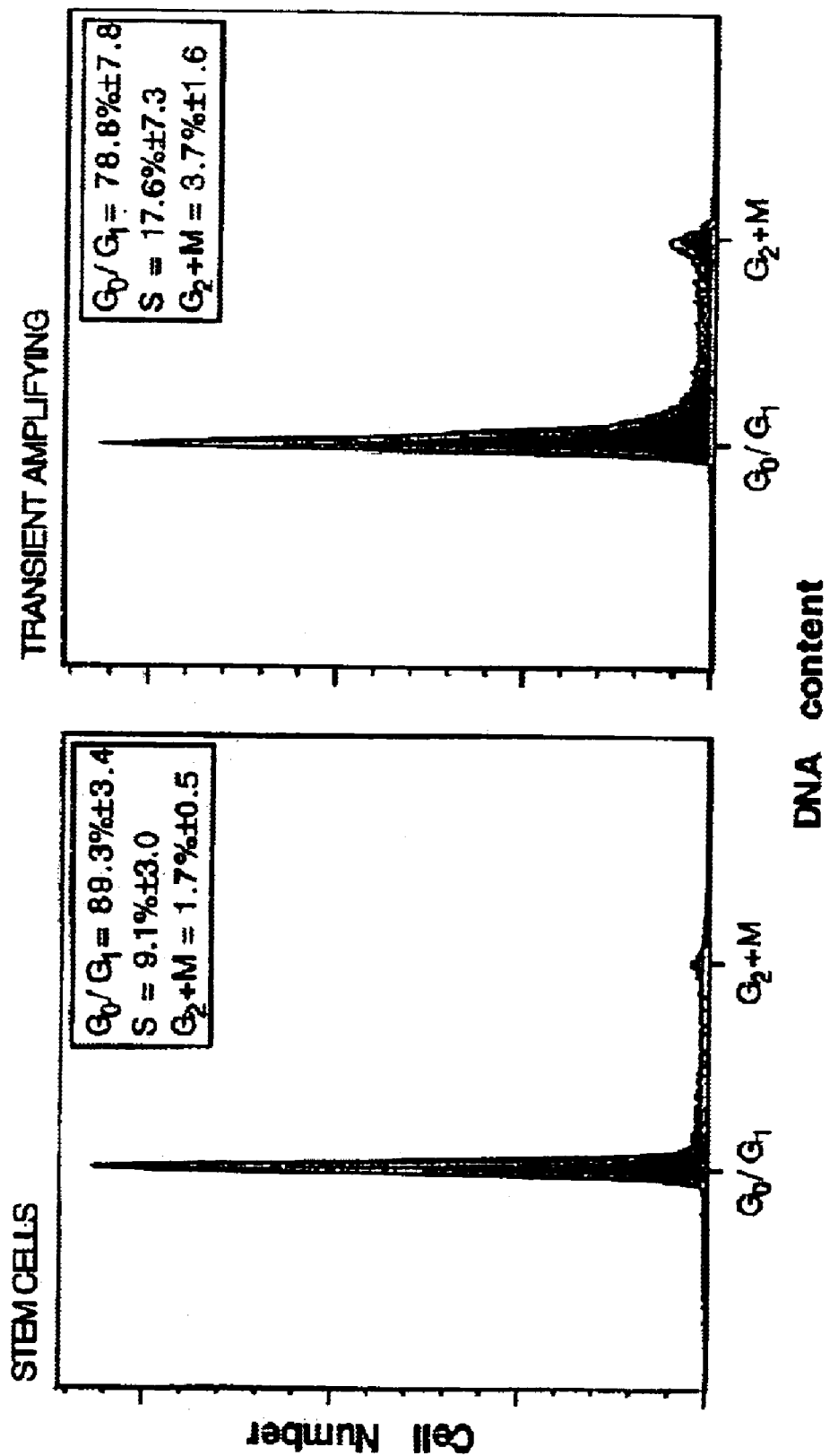
FIG. 2. Cell cycle profile of sorted stem and TA cells.

[+]Mouse ear epidermal cells were dissociated, stained with Hoechst and propidium iodide, and sorted into three populations with an EPICS 753 flow cytometer
[^]Mean ± standard deviation for 6 experiments
[*]% LRCs = % of each group that were BrdU label-retaining cells The Majority of Stem Cells Show a G0/G1 Cell Cycle Profile In order to determine whether there was a difference in the cell cycle profile between the stem and the TA sorted populations, cells from each population were stained with hypotonic propidium iodide, and DNA content determined by FACScan flow cytometry. The cell cycle profiles obtained were clearly different (FIG. 2, Table 2). As expected, most of the cells in both populations showed a 2 n amount of DNA, clearly showing that they were in G1. Quantitation of the stem cell profile revealed that about 90% were in G1 with only 9% in S, and 1.5% in G2/M, whereas the TA cells showed a more typical neonate profile of 79% in G1, 17% in S, and 4% in G2/M. These data show quantitatively that the majority of stem cells are somehow held in G0/G1 and that twice as many TA cells versus stem cells are dividing, hence their name amplifying. Control profiles from total adult skin basal cells were 92% G1, 6% S, and 1.4% G2/M and total neonate skin basal cells were 80% G1, 16% S, 3% G2/M (Table 2).

TABLE 2

| Cell Type | G0/G1 | S | G2/M |
|---|---|---|---|
| Adult ear basal (n = 3) | 92.0 ± 1.7 | 6.6 ± 1.7 | 1.4 ± 0.2 |
| Neonate basal (n = 3) | 80.5 ± 4.3 | 16.4 ± 4.1 | 3.1 ± 1.0 |
| Transient Amplifying (n = 4) | 78.8 ± 7.8 | 17.6 ± 7.3 | 3.7 ± 1.6 |
| Stem (n = 4) | 89.3 ± 3.4 | 9.1 ± 3.0 | 1.7 ± 0.5 |

Mean ± standard deviation

Only Stem Cells Form Large Maintainable Undifferentiated Colonies in Culture

Figure 3:
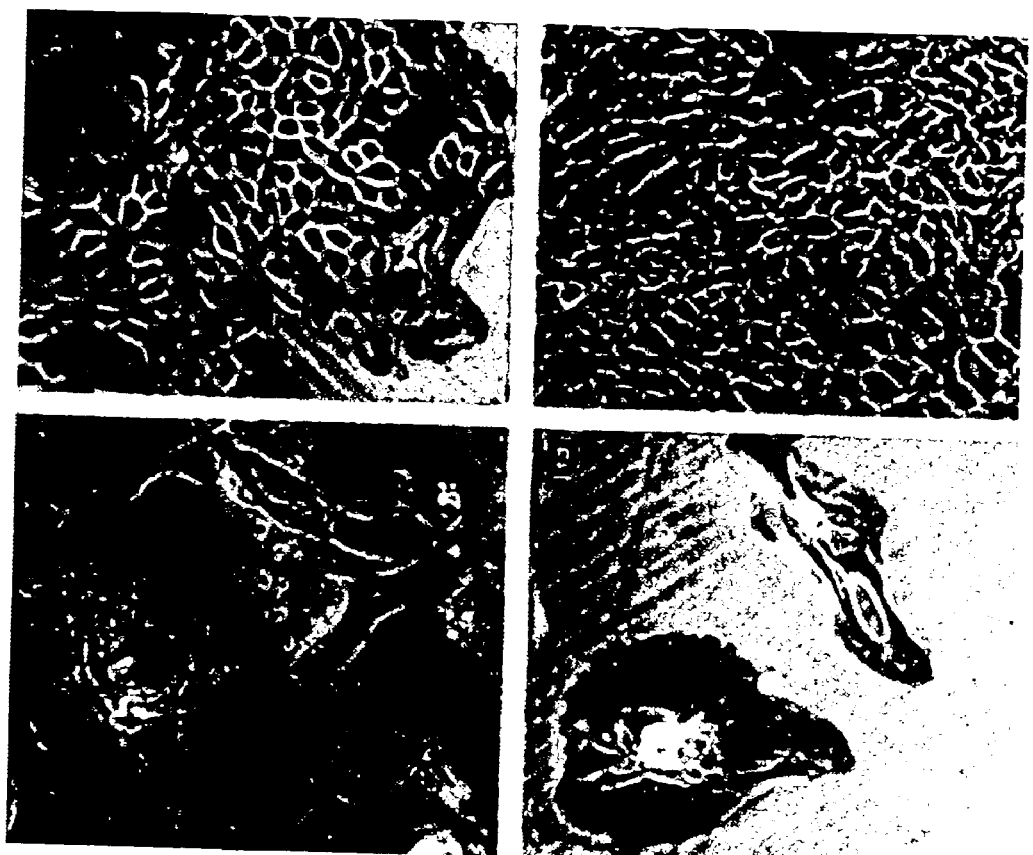
FIG. 3. Phase contrast photograph of sorted cells in culture. (A) Passage 0 of stem cells cultured for 7 days. (B) Passage 8 of stem cells, 7 day culture. (C) Passage 0 of TA cells, 7 day culture. (D) Passage 1 of TA cells, 7 day culture.

After the physical stress of sorting, both the stem and TA cells required a higher than normal concentration of cells to grow in culture ($5 \times 10^5$ cells per 35 mm dish). The TA cells grew relatively rapidly, reaching confluence in approximately 7 days. The stem cells, on the other hand, grew more slowly at first, taking at least 12 days to reach confluence, suggesting that stem cells may be slower to enter a proliferative phase than transient amplifying cells. This observation agrees with the cell cycle profiles described above, which show that twice as many TA cells are proliferating as compared to stem cells. The morphology of the initial cultures was also different, with the stem cells maintaining a small undifferentiated phenotype and the TA cells forming larger cells with fewer cells per colony (FIG. 3). The TA cells produced around 3 population doublings in the initial plating, and after the first passage, they divided at least twice then differentiated and lifted off the dish (FIG. 3D), demonstrating that the cells in this sorted population have a finite number of cell divisions that they can perform. In contrast, the stem cell population may be capable of unlimited cell divisions. The sorted stem cells did not differentiate in culture, but instead remained as small undifferentiated cells (FIG. 3B) until the experiment was stopped at passage 19 (57 population doublings), which is approximately double what Hayflick predicted (Hayflick, 1965).

Both Stem and Transient Amplifying Cells Express an Integrated Recombinant Gene

Figure 4:
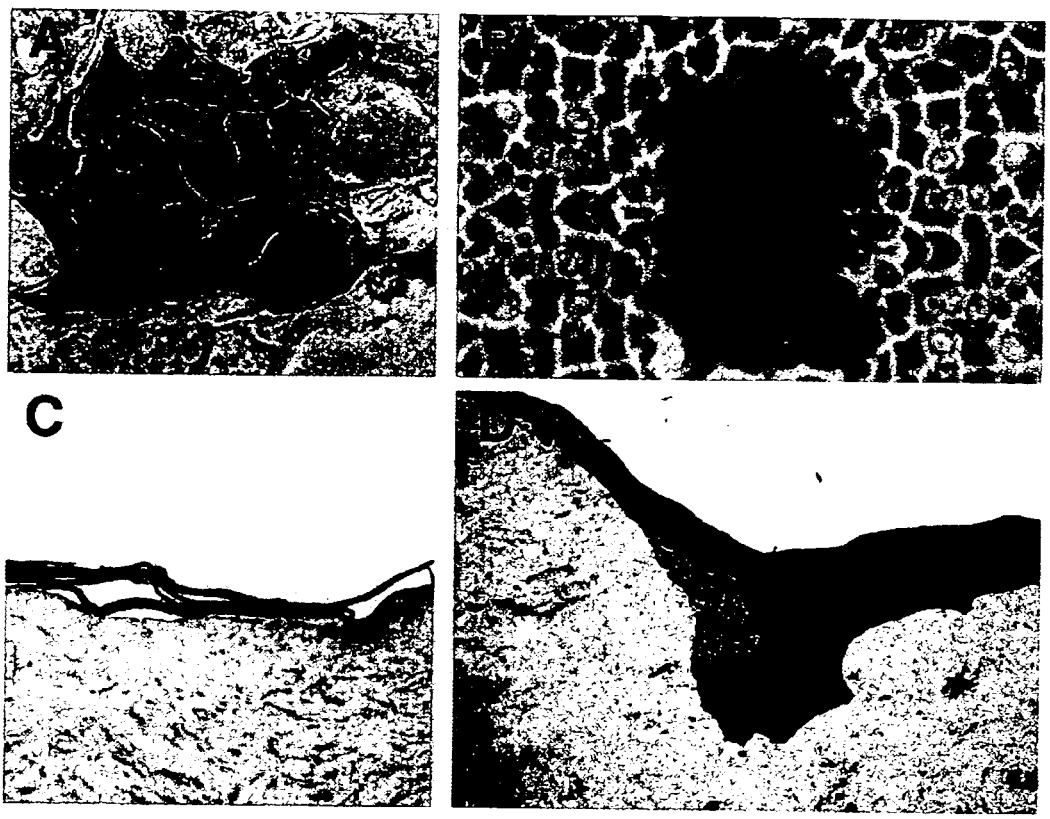
FIG. 4. Sorted mouse TA and stem cells transduced with retroviral-LacZ. Both TA (A) and stem (B) cells formed gal+ colonies in submerged monolayer cultures. Epidermis was engineered by growing either TA or stem cells on collagen gels with skin fibroblasts. (C) Epidermis from TA after 2 months. (D) Epidermis from stem after 6 months. A and B are phase contrast photographs of x-gal stained cultures. C and D are 1 plastic epon sections stained with Richardson's stain (Hayat, 1972).

To introduce recombinant genes into epidermal stem cells one must either achieve 100% transfection efficiency in a population of total basal cells (Choate, 1997; Dellambra, 1998), which contains a few stem cells, or separate the stem cells from the transient amplifying cells before transfection. Cultures of sorted stem and TA cells showed a similar propensity for transduction with the retrovirus, both giving around a 15% transduction efficiency of 48–72 hour cultures. 5 days after transduction, both stem and TA cultures showed colonies of βgal+cells (FIG. 4), and both maintained their identifying morphology after transduction.

Only Stem Cells Show the Ability to Recapitulate an Epidermis and Show Long Term Expression of an Integrated Recombinant Gene in Bioengineered Epidermis For isolated keratinocytes to form a structurally complete epithelium, the cells must be grown on a connective tissue or with fibroblasts (Rheinwald, 1975; Mackenzie, 1984; Mackenzie, 1993). To test whether the sorted stem cells and the sorted TA cells had the capacity to reform a complete epidermis without the other cell type, each population was used separately to bioengineer an epidermis in combination with a collagen type I gel containing neonate mouse skin fibroblasts. In order to test long term gene expression, colonies from either the stem or the TA sorted cell populations that had been transduced with a retroviral-LacZ reporter gene were used. Both the TA and the stem colonies adhered to the collagen gel, and both appeared to be maintaining an epidermis by gross examination. However, at the two month sampling time, it became apparent that only the stem cells were maintaining a complete morphologic epidermis. The TA cells had completely differentiated, showing only thin, ribbon-like layers of stratum corneum cells, some of which were still βgal+ (FIG. 4C). The bioengineered tissues made from the sorted stem cells demonstrated both epidermal proliferation and differentiation, producing a morphologically normal neonate mouse epidermis (FIG. 4D). In this study cultures with both transduced and nontransduced cells were lifted onto the bioengineered collagen gels, yielding a bioengineered epidermis with both βgal+ and βgal− cells, as can been seen in FIG. 4D. Large areas of the tissue bioengineered from the stem cells remained βgal+ for six months, suggesting that using transduced epidermal stem cells to bioengineer an epidermis yields a tissue with long term recombinant gene expression.

Discussion

It is generally agreed that homeostasis of continuously renewing tissues, such as the epidermis, is maintained by stem cells. These cells are thought to be undifferentiated cells that divide to produce daughter cells that maintain the stem cell phenotype and daughter cells that undergo a finite number of cell divisions before they differentiate and leave the proliferative compartment. Only the stem cells persist throughout the lifetime of the organism (Cairns, 1975). Although stem cells are considered to progress through the cell cycle at a slower rate than transient amplifying (TA) basal cells, they have a higher proliferative potential, and it is thought that they increase their proliferative rate at times of tissue regeneration, such as during fetal development and wound healing (for review see Cairnie, 1976; Potten, 1997). The heterogeneity in the epithelial basal cell compartment was first demonstrated in 1981, when a small subpopulation of label-retaining cells (LRCs) was identified in various mouse epithelia. These cells retained a tritiated thymidine label for up to ninety days (Bickenbach, 1981). LRCs were shown to have had the stem cell characteristics of immaturity in that they were smaller and contained few organelles, that they were clonogenic, and that they were slowly cycling (Bickenbach, 1981). This label-retention method has been used for the last two decades to localize stem cell populations in hamster epidermis and oral mucosa (Bickenbach, 1984), monkey palmar (Lavker, 1982), and limbal (Cotsarelis, 1989) epithelia, the bulge region in hair follicles (Cotsarelis, 1990), and human adult palmar (Lavker, 1982), and fetal epidermis (Bickenbach, 1987). However, this method only identifies stem cells; it does not allow for separation of stem cells from other proliferative cells. Isolating a pure population of epidermal stem cells has become increasingly important as gene therapies for inherited skin disorders become more feasible. In this study, a cell sorting method was employed that results in a virtually pure population of LRCs, the putative epidermal stem cells.

These sorted cells show the growth and repopulation potential expected for stem cells, and these cells show long term expression of a retroviral transduced LacZ recombinant gene, both in submerged cell culture and in bioengineered skin.

Epidermal Stem Cell Markers

Previously, Jones et al. proposed that epidermal stem cells expressed a higher level of 1 integrin on their cell surface than did the transient amplifying cells (Jones, 1995; Jones, 1994). This study was based on the postulate that when basal cells become committed to the differentiation pathway, they down-regulate integrins in their cell membranes, making them less adherent to the components in the basement membrane. A colony forming efficiency assay of these cells demonstrated that rapid adhesion to the integrin ligand collagen type IV resulted in large colonies in vitro. It was later confirmed that rapid adherence was a good first step to selecting a pure population of epidermal stem cells, but that the ligand used made no difference, suggesting that stem cells could not be cleanly separated from transient amplifying cells by expression of a specific integrin (Bickenbach, 1998). Other cell surface markers have been found that distinguish hematopoietic (Spangrude, 1988; Bernstein, 1994), liver (Brill, 1993), and mast stem cells (Durand, 1994), but so far no single cell surface marker has been found to separate a pure population of epidermal stem cells from the transient amplifying cells. Two studies have reported that by using a combination of markers they could enrich stem cell population. The first study was based on a cell surface monoclonal antibody that differentially stained proliferative basal cells so that they could be sorted by FACS according to how brightly they were stained (Mackenzie, 1989). The second study used high expression of α-integrin and low expression of a proliferative associated cell surface marker and resulted in an epidermal population highly enriched for proliferative cells (Li, 1998). Several years ago, Michel et al. found that an antibody to keratin K19 preferentially stained a subpopulation of cells in the hair follicle bulge that contained the follicular LRCs (Michel, 1996). More recently, it was reported that the antibody C8/144B originally generated against a short CD8 peptide also stained a subset of K15 expressing cells in the human hair follicle bulge (Lyle, 1998) that might be the follicular stem cell population. Others using specific K15 antibodies found staining in all basal cells in human (Waseem, 1999) and sheep (Whitbread, 1998) epidermis. To overcome the lack of a stem cell marker, a different approach was employed herein, in which a previously published hematopoietic method (Goodell, 1996) was modified to yield a virtually pure population of label-retaining cells, the putative epidermal stem cell population.

Stem Cell Clonogenicity and Cell Cycle Characteristics

Evidence suggests that the size of the cell may be a determinant in the clone-forming ability of keratinocytes, with the smallest cells forming the largest clones (Barrandon, 1985; Barrandon, 1986). In rat epidermis, small keratinocytes which were Ki67 negative (putatively in G0 of the cell cycle) formed small initial clones, but formed very large subclones, thereby indicating maintenance of a high clonogenic efficiency and possibly self-renewal. Both characteristics are indicative of stem cells (Pavlovitch, 1991). In human epidermis, cells less than eleven microns in diameter maintained their division capability for several passages in culture, and the clones from such cells were able to be better expanded, thereby containing more cells, than clones from larger cells (Barrandon, 1985). Such cultured clones have been used to form permanent coverage of large burn wounds (De Luca, 1989), suggesting that the clones contained stem cells. In this study, the sorted stem cells formed larger colonies than did the TA cells, and the cells growing in the stem cell colonies appeared smaller than those in the TA colonies. However, when cells were sorted based only on size, both stem and TA cells were found in the small populations, suggesting that size alone cannot be used to sort a pure population of stem cells.

For years stem cells have been described as slow cycling (Lajtha, 1979). In support of this theory, a small subpopulation of keratinocytes was shown to retain nuclear label for a very long period of time (Bickenbach, 1981). As further support, a very slowly cycling subpopulation of epidermal cells has been recently identified in the hair follicles of adult mice (Morris, 1999). This implies that there is a subpopulation of basal cells that progress through the cell cycle at a different rate than their neighboring cells. It has been assumed that these cells are quiescent or held in the G0 phase of the cell cycle. Cell cycle analysis of bone marrow stem cells showed that they were quiescent (Veer Reddy, 1997), with most of them held in G0 as judged by the amount of RNA and DNA in the cells (Gothot, 1997). The analyses of sorted stem and TA cell populations described herein concur with this finding, that the majority of stem cells reside in the G0/G1 phase of the cell cycle, whereas twice as many TA cells are actively cycling.

Implications for Tissue Engineering and Gene Therapy

Although several studies have reported introduction of recombinant genes into continuously renewing epithelial tissues (Sanes, 1989; Garlick, 1991), in most cases long term gene expression was not achieved (Morgan, 1987; Sanes, 1989; Garlick, 1991; Vogt, 1994; Fenjives, 1996). It did not matter whether the gene transfer technique involved shooting the DNA directly into the tissue via a gene gun or transfecting cultured epithelial cells then grafting the transfected cells to host animals. In the few studies that reported long term gene expression, only very few basal cells continued to express the transduced recombinant gene for longer than two months (Flowers, 1990; Mackenzie, 1997; Deng, 1997; Ghazizadeh, 1999), suggesting that transducing stem cells, whether in a tissue or in culture, is difficult and not efficient.

To introduce recombinant genes into stem cells one must either achieve 100% transfection/transduction efficiency in a population of total basal cells (Choate, 1997; Dellambra, 1998), or separate the stem cells from the transient amplifying cells before transfection/transduction. The first method is most commonly used, but it appears to transfect/transduce very few stem cells, probably because there are very few stem cells in the total population. Various enrichment procedures can result in substantial enrichment of stem cells.

Human keratinocytes were enriched for stem cells by rapid adherence to collagen type IV. These enriched cells were transduced with a retroviral vector carrying the LacZ reporter gene and showed persistent expression of gal in submerged culture and throughout twelve weeks of growth in organotypic culture (Bickenbach, 1999). Using the sorting method described herein, pure populations of stem and TA cells were prepared and both the stem and the TA cells were transduced with an efficiency of 15%. Moreover, both populations expressed the recombinant gene in a submerged monolayer culture. However, when used to bioengineer a skin, only the epidermis engineered from the stem cells was maintained. The epidermis from the TA cells had completely differentiated by two months. Although both cell types showed expression of the recombinant gene, only the stem cells showed long term (six months) expression in the bioengineered skin. Thus, pre-selection of stem cells is not only possible, but that it is a reasonable first step for future gene therapy strategies for genetic skin diseases.

Example 2

Homeostasis of the hematopoietic system, like the epidermis, is maintained by somatic stem cells which give rise to stem cells and TA cells. TA cells undergo a finite number of cell divisions before differentiating and leaving the proliferative compartment, whereas the stem cells persist throughout the lifetime of the organism (Cairns, 1975). Recently it was demonstrated that these adult somatic stem cells have the remarkable capacity to differentiate into other tissue types (Jackson, 1999), and have a plasticity only expected of embryonic stem cells. As described below, epidermal stem cells also have such tissue plasticity, and differentiate into mesenchymally-derived tissues, such as adipose and hematopoietic tissues.

I. Administration of Epidermal Stem Cells To Lethally-Irradiated Mice

Materials and Methods

Epidermal Stem Cell Isolation

Skin samples obtained from neonate or adult C57BL/6-EGFP mice are incubated in 0.25% Trypsin or Dispase II overnight at 4 C., the epidermis removed from the dermis, and the basal cells dissociated by gently shaking the epidermis in 0.25% trypsin. The dissociated basal cells are centrifuged and resuspended at $5 \times 10^6$ cells/ml in SMEM (Life Technologies, Grand Island, N.Y., USA) with 0.05 mM $Ca^{++}$, 2% chelexed FBS, 1mM Hepes, 1% pen-strep, and 5 $\mu$g/ml Hoechst 33342. Cells are incubated at 37 C. for 90 minutes, centrifuged and resuspended in 1 $\mu$g/ml propidium iodide in SMEM and kept on ice until the flow cytometric procedure. Cell sorting is performed on a Coulter EPICS 753. Forward and orthogonal scatter signals are generated using 100 mW @ 488 nm. Hoechst 33342 and propidium iodide are excited with 100 mW of UV (351–364 nm). Hoechst fluorescence is measured through a 440/60 nm bandpass filter while propidium iodide is measured through a 670/14 run bandpass filter. All parameters are collected using linear amplification in listmode. Stem cells are sorted using gates placed around the population exhibiting low to medium forward and orthogonal scatter, and low Hoechst and propidium iodide fluorescence.

DNA Isolation and PCR Detection of EGFP in Cells or Tissues

Cells are resuspended in lysis buffer (0.32 M sucrose, 10 mM Tris-HCl (pH 7.5), 5 mM $MgCl_2$, 1% (v/v) Triton X-100), centrifuged, then resuspended in PBND buffer (50 mM KCl, 10 mM Tris-HCl (pH 8.3), 1.5 mM MgCl, 0.45%(v/v) Nonidet P-40, 0.45% (v/v) Tween 20) with 60 $\mu$g/ml proteinase K (Roche) in 10 mM Tris-HCl (pH 7.5), incubated at 55° C. for 60 minutes, then heated to 97° C. for 10 minutes to inactivate the proteinase K. Five hundred ng (for blood) or 1000 ng (for bone marrow) of DNA is used per 20 $\mu$l PCR reaction.

Nested primers may be used in two separate PCR reactions to detect EGFP. The first set (5'AAG TTC ATC TGC ACC ACC G 3' (SEQ ID NO: 1), 5' TGC TCA GGT AGT GGT TGT CG 3' (SEQ ID NO: 2)) is designed to prime 475 bp of the EGFP gene. The second set of primers (5° CGA CCA CAT GAA GCA GCA CG 3' (SEQ ID NO: 3), 5' GTT CTG CTG GTA GTG GTC GG 3' (SEQ ID NO: 4)) is just inside the first set of primers and designed to prime 331 bp. The first PCR is 37 cycles (90 seconds at 94° C., then 12 cycles of 20 seconds at 94° C., 30 seconds at 64° C. (with a reduction of 0.5° C. per cycle), 35 seconds at 72° C., then 25 cycles of 20 seconds at 94° C. 30 seconds at 58° C., 35 seconds at 72° C., then 5 minutes at 72° C.). To run the second PCR, 2 1 of the first PCR product is used. The second PCR is 37 cycles (90 seconds at 94° C., then 12 cycles of 20 seconds at 94° C., 30 seconds at 68° C., 35 seconds at 72° C., then 25 cycles of 20 seconds at 94° C., 30 seconds at 62° C. (with a reduction of 0.5° C. per cycle), 35 seconds at 72° C., then 5 minutes at 72° C.).

Experimental Design

Approximately 24 hours before transplantation of cells, C57BL/6 mice are conditioned with 1100 rad whole body irradiation from a $^{137}Cs$ source. The total irradiation is divided into 2 separate doses, i.e., first 600 rad, then 500 rad 3 hours later. During the first 2 months after irradiation, the mice are housed in isolated microcages, and antibiotics are given in their drinking water.

Epidermal stem cells, TA cells, and total cells are isolated from back skin of C57BL/6-EGFP neonatal mice. Bone marrow cells are isolated from adult C57BL/6 mice. Three groups of mice receive epidermal cells (stem, TA, total)+ bone marrow cells for radioprotection. A control group receives $2 \times 10^5$ bone marrow cells alone. The cells are injected as follows:

$1 \times 10^6$ epidermal cells (Epi)+$1 \times 10^{104}$ bone marrow cells (BM) into 5 mice for each group (stem, TA, total)

$5 \times 10^5$Epi+$1 \times 10^4$ BM $1 \times 10^5$Epi+$1 \times 10^4$ BM

The best combination of cells is chosen, e.g., whichever combination produces the greatest number of GFP+ cells in the bone marrow and in the circulating blood. Then the test is repeated with a lower number (e.g., $1 \times 10^3$) of BM cells to determine whether epidermal stem cells can also provide radioprotection. However, if the best scheme for bone marrow differs from that for blood, then the bone marrow scheme is chosen.

The mice are bled at 1, 2, 4, and 6 months after injection. The blood cells are analyzed for GFP expression. GFP+ cells are examined for expression of keratin K14 to determine if epidermal stem cells retain their epidermal distinction. The percentage of GFP+ cells in the blood is also calculated.

Six months after injection blood, bone marrow, liver, and other tissues, e.g., brain, pancreas, and lung, are harvested and analyzed for GFP expression. GFP+ cells are examined for K14 expression. The percent survival for each injected group is also noted.

Sample Processing

Blood samples are withdrawn from each mouse by retro-orbital bleeding. Bone marrow is harvested from femurs and tibias. To determine EGFP expression and cell phenotypes, blood samples are collected in 3 ml of RPMI 1640 medium containing 0.5 U/ml of heparin. After washing once with PBS, the red blood cells are eliminated using ACK lysis buffer. Following washing twice with PBS containing 3% of FBS, the cells for FACS analysis are stained with biotin-labeled mouse hematopoietic lineage specific antibodies, followed by streptavidin-PE staining. EGFP and PE fluorescence analyses are performed by CELLQuest software using a FACScan (Becton Dickinson). Cells for microscopic analysis are spread onto coated slides, air-dried, and stored at 4° C. until stained with antibodies.

Tissue samples are bisected with a sharp razor blade or scalpel. One piece is fixed in 4% paraformaldehyde and embedded in paraffin (a processing method that does not affect the GFP fluorescence, but gives good histology), and the other is cryoprotected in 30% sucrose, then frozen in OCT for antibody analysis by immunofluorescence of sections. OCT freezing allows visualization of GFP, and most antibodies will stain frozen sections, but the histology is not very good. A small piece of tissue is placed in DNA isolation buffer for PCR amplification of the EGFP gene.

Cells or liver sections are deparafinized and examined for EGFP expressing cells using a Nikon Eclipse E600 microscope with epifluorescence. In the blood and bone marrow cell smears, the number of GFP+ cells and total number of cells is counted and the percentage of GFP$^+$ cells calculated for each mouse at each time point. A total of 20,000 cells on each slide is counted, the mean and standard error determined, and analysis of variance (ANOVA) performed to determine significant differences.

Results and Discussion

To determine whether somatic epidermal stem cells can function in a similar manner to or substitute for hematopoietic stem cells, somatic epidermal stem cells were administered to lethally-irradiated mice. Epidermal stem cells were isolated from the back skin of C57BL/6 neonatal mice which carry the EGFP gene (C57BL/6-EGFP), then injected into the tail veins of C57BL/6 mice which received a total of 1100 rads of -irradiation to lethally ablate their hematopoietic system. Using histology, immunofluorescence, and expression of specific differentiation or lineage markers, the presence and contribution of GFP-marked epidermal stem cells to the reconstituted bone marrow is determined. Further, the epidermal differentiation markers or bone marrow or blood cell lineage markers are used to determine whether GFP-marked cells have altered their phenotype.

Based on preliminary data, GFP$^+$ cells were expected to be found in the circulating blood at each time point, and in the bone marrow from mice receiving stem cells. Thus, GFP$^+$ epidermal stem cells are likely found in other tissues, and so could have the capacity to replenish the hematopoietic cell lineages. The data also demonstrated that epidermal stem cells have tissue plasticity, i.e., they may be pluripotent, and can engraft into and likely differentiate into mesenchymally-derived tissues, such as adipose and hematopoietic tissue. This suggests that epidermal stem cells can substitute for hematopoietic stem cells. Since the skin is the largest organ in the body, and epidermal stem cells can readily be obtained from a simple skin biopsy, the skin could then provide a large renewable source of generic stem cells. These cells may express markers from the tissue or the hematopoietic system. However, epidermal stem cells may be capable of reconstituting the bone marrow and altering their phenotype in response to their environment. If epidermal stem cells are truly pluripotent, the advantage could be tremendous.

II. Reconstitution of Tissues with Epidermal Stem Cells
Materials and Methods
Sample processing Blood, bone marrow, and tissues are harvested and processed as described above. GFP$^+$ cells are phenotyped with antibodies to hematopoietic cell lineages, and, in the case of liver, to hepatocyte markers. For these experiments, secondary antibodies are conjugated to Cy5 or streptavidin-Texas red so that immunolabeled and GFP$^+$ cells can be visualized simultaneously using fluorescence or confocal microscopy. DAPI staining is used to delineate nuclei. The cells for FACS analysis are stained with biotin-labeled mouse lineage specific antibodies, followed by streptavidin-PE staining. For each cell type, the total number of cells and the percentage of each cell type that is GFP$^+$ is determined.

Antibodies for Cell Phenotyping

Bone marrow stem cell markers include Sca-1 and c-Kit (CD 117), but lack any lineage-specific markers (Lin-) characteristic of B cells (B220, CD45R), granulocytes (Gr-1), myelomonocytic cells (Mac-1), and T cells (CD3, CD4 and CD8). Antibodies for these markers are commercially available from PharMingen.

Surface markers characteristic of mature blood cells are commercially available from PharMingen, for example, for B lymphocytes, CD45R (B220); T lymphocytes, CD5 (Ly-1) or CD3, CD4, CD8; erythroid cells; TER119, granulocytes; Gr-1, and myelomonocytic cells, CD11 b (Mac-1). Hepatocyte markers include cell—cell adhesion molecule (c-cam) and albumin. Liver can be stained immunohistochemically with the polyclonal rabbit antibody against albumin (Accurate Chemical), dipeptidyl peptidase IV/CD26 (PharMingen) or E-cadherin (Zymed). Epidermal basal cells, including stem and TA cells, can be identified by expression of keratin K14 (Anti-K14 from Babco).

Sample Analysis

To determine whether epidermal stem cells repopulate lethally-irradiated mice with circulating blood cells of all or multiple hematopoietic lineages, GFP+ cells found in the circulating blood, the bone marrow, and other tissues are analyzed for expression of keratin K14 and for hematopoietic lineage differentiation markers via FACS, PCR, and microscopic immunofluorescence. The percentage of GFP+ cells is calculated for each antibody used.

Samples obtained six months after injection, e.g., from bone marrow, liver, and other tissues, are also analyzed for GFP expression. Other tissues, such as brain, pancreas, and lung are sectioned and examined for GFP+ expression. If GFP+ expressing cells are found, the tissue is stained with an appropriate antibody for the tissue to determine whether the GFP$^+$ cells have altered their phenotype. Percent survival for each injected group is also determined.

Discussion

GFP$^+$ epidermal stem cells are likely found in other tissues, such as the liver, and so skin may be a source of generic stem cells.

III. Engraftment of Epidermal Stem Cells in the Bone Marrow Method

To determine whether epidermal stem cells can function as bone marrow cells for the life span of the recipient and whether they alter the life span, the mice described above are followed for at least 18 months or until near death, then the blood, bone marrow, and tissues are harvested and analyzed for GFP expressing cells and hematopoietic lineage cells.

For the secondary transplantation, bone marrow from mice engrafted for six months is isolated, the GFP$^+$ cells sorted via FACS, then used to reconstitute another group of lethally-irradiated C57BL/6 mice via tail vein injection. A group of 5 mice is injected with the isolated GFP+ cells from the first transplanted group. Blood from the second set of mice is drawn 1, 2, and 6 months after injection. At 6 months, the blood bone marrow and other tissues are harvested, processed, and analyzed, as described above.

The percent GFP+ cells in the circulating blood, the bone marrow, and the liver and other tissues is determined, and compared by student's paired t-test to the percent determined for each cell or tissue type for primary recipients. For survival, a group of 5 mice each (stem-injected, TA-injected, total-injected, $1^{st}$ control, and $2^{nd}$ control) is allowed to live out their normal life span. The two controls are: 1) C57BL/6 mice who have received no irradiation or cells; and 2) C57BL/6 mice who have been irradiated and injected with $1 \times 10^5$ C57BL/6 bone marrow cells only (no epidermal cells). Survival rates for each group is compared by analysis of variance (ANOVA).

Results

The data suggest that epidermal stem cells engraft into the bone marrow of lethally-irradiated mice, and have the capacity to replenish the hematopoietic cell lineages. These cells were found in the bone marrow at 15 weeks post-administration. Thus, these cells most likely function up to the death of the recipient. Therefore, the skin could be used as a source of generic stem cells. It is likely that mice who receive enough epidermal stem cells to produce the appropriate amount of hematopoietic lineage cells will live a normal life span. If epidermal stem cells replace the function of hematopoietic stem cells, then they should be able to reconstitute a second set of mice (secondary transplantation), who also live a normal life.

IV. Expression of a Therapeutic Gene by Epidermal Stem Cells

Production of factor VIII is not necessarily tissue restricted. A variety of cells types, including skin fibroblasts (Hoeben, 1990), and epidermal keratinocytes (Fakhazaden, 2000), have been shown to process and secrete factor VIII in vitro and in vivo. Thus, transduced epidermal stem cells could be used as a stable source to express therapeutic levels of factor VIII.

Materials and Methods

ELISA

Briefly, 96-well immunoplates are coated with two murine monoclonal anti-human FVIII antibodies, i.e., monoclonal antibody against human FVIII:c light chain from Boehringer Mannheim and ESH 5 monoclonal antibody against human FVIII:c A1 heavy chain from American Diagnostica. Horseradish peroxidase-conjugated ESH 8 monoclonal antibody specific for human FVIII:c C2 domain is used as the secondary antibody to detect bound FVIII antigen. Recombinant FVIII from Baxter Healthcare Corporation or pooled normal human plasma is used as for the standard curve ranging from 0.61 to 79 ng/ml. The sensitivity of this assay to detect human factor VIII in mouse plasma is 0.3 ng/ml and this assay has no cross-reaction with mouse factor VIII.

Coamatic® Coamatic® Factor VIII kits obtained from Chromogenix Instrumentation Laboratory SpA (Milano, Italy) are used to measure factor VIII activity. A low range microplate method is used throughout. This method has a detection limit of 0.005 IU/ml of factor VIII. In the presence of calcium ions and phospholipids, factor X is activated to factor Xa by factor IXa. This activation is greatly stimulated by factor VIII which acts as a cofactor in this reaction. By using optimal amounts of calcium, phospholipid and factor IXa, and an excess of factor X, the rate of activation of factor X is linearly related to the amount of factor VIII. Factor Xa hydrolyses the chromogenic substrate S-2765 thus liberating the chromophoric group, pNA. The color is then read photometrically at 405 nm.

Transduction of Epidermal Stem Cells

Epidermal stem cells are isolated from C57BL/6 neonatal mouse back skin, and the cells are plated on culture dishes coated with collagen type IV in N-medium. The cells are allowed to grow for 48 hours at 36.5° C. in a $CO_2$ incubator. To determine best transduction efficiency, 5 cultures of epidermal stem cells are transduced with FIV-EGFP, using 5 µg/ml polybrene and increasing MOIs (e.g., 1–80). Envelopes that are available for transduction of epidermal stem cells with FIV other than VSV-G include amphotropic, RD114, GALV, Ross River Virus, and Semliki Forest virus envelope. Self-activating lentiviral vectors incorporate the woodchuck posttranscriptional regulatory element (WPRE), and the central polypurine tract (cPPT).

After ex vivo transduction, the cells are removed from the culture dish by treatment with 0.25% trypsin for 10 minutes at 37° C., counted and resuspended for injection. The transduced epidermal stem cells and $1 \times 10^4$ bone marrow cells (for radioprotection) are injected into the tail veins of 10 irradiated C57BL/6-FVIII–/– mice.

Sample Processing and Analysis

The transduced cells and control cells are permitted to grow for 48 hours after adding FIV-EGFP, then the medium is changed. The number of fluorescent and non fluorescent cells is counted using a Nikon phase microscope equipped with epifluorescence, and the percentage of GFP+ cells for each MOI is calculated. Cultures are monitored for cell death by counting the number of cells in the supernatant at 48 hours, and at 4, 7, and 14 days. A mean and standard error is determined for each MOI and the mean number of dead cells/MOI determined. The MOI that yields the highest efficiency and the least cell death is used for transducing FIV-huFVIII to epidermal stem cells in subsequent experiments.

After transducing with FIV-huFVIII, it is determined whether epidermal stem cells secrete human factor VIII. Supernatant from each of 5 cultures is collected at 48 hours, and at 2, 4, 7, 14, and 21 days after transduction and subjected to human FVIII specific capture ELISA assay. The amount of human factor VIII in ng/ml is determined by comparison to a standard curve.

After tail vein injection, thrombin is applied topically to stop bleeding. Control mice receive only bone marrow cells. Blood is withdrawn at 1, 2, 4, and 6 months after injection, red blood cells are lysed, the blood is centrifuged to separate plasma from the cells, and the amount of huFVIII is measured via human specific capture ELISA assay. The amount of human factor VIII (ng/ml) is determined by comparison to a standard curve (recombinant FVIII from Baxter Healthcare Corporation ranging from 0.61 to 79 ng/ml). The huFVIII level of each mouse is expressed as ng/ml and compared via ANOVA. The activity of the huFVIII in the plasma is determined by Coamatic® Factor VIII kits obtained from Chromogenix Instrumentation Laboratory. As a functional test, the phenotypic correction of the injected hemophilia A mice for rates of blood loss and survival after tail clipping is examined, and the length of time it takes the blood to clot is measured. At 6 months, each mouse that shows at least 2 ng/ml huFVIII is tested by tail clipping. The tails are clipped and allowed to bleed. The amount of blood lost, the survival, and the time for blood to clot is measured and compared to the amount of huFVIII measured in the plasma of each mouse.

Results

If epidermal stem cells can replace hematopoietic stem cells in repopulating the blood with a full complement of cell lineages, then it may be possible for epidermal stem cells to be used for a variety of therapies. To determine whether epidermal stem cells can serve as a stable source for the expression of a secreted therapeutic gene product, the hemophilia A factor VIII deficient mouse model was used. Hemophilia A factor VIII deficient mice provide a model of a disease characterized by the lack a secreted protein. Notably, only a 5% replacement of factor VIII is necessary to move from a severe to a mild form of the disease. Thus, this is a good model for an alternative stem cell therapy. The hemophilia A FVIII-/- mice have been backcrossed onto the C57BL/6 background for several generations. Thus, these mice are considered to be syngeneic to the EGFP transgenic mice that are also on C57BL/6 background.

Epidermal stem cells were isolated from C57BL/6 neonatal mice, and transduced with FIV-huFVIII ex vivo, which has been shown to be processed and secreted by hematopoietic progenitor cells. The transduced epidermal stem cells were grown in culture and huFVIII secretion levels determined, then the cells are injected into lethally-irradiated C57BL/6-FVIII deficient mice and the plasma levels of human factor VIII determined. Two complementary assays can be used to measure factor VIII activity (human FVIII specific capture ELISA and Coamatic® Factor VIII kit).

Based on preliminary data, increasing the MOI likely improves transduction efficiency of epidermal stem cells with FIV-EGFP to >50%, perhaps as much as 80%. Moreover, transduced epidermal stem cells process and secrete factor VIII into the culture supernatant. Based upon data that hematopoietic progenitors process and secrete factor VIII after transduction with FIV-huFVIII, and the knowledge that keratinocytes have been previously shown to secrete detectable levels of factor VIII into the plasma of mice (Fakharzaden, 2000), transduced epidermal stem cells likely process and secrete detectable levels of huFVIII into the plasma of the hemophilia A factor VIII deficient mice. If levels>5 ng/ml are found in the plasma, the mice are expected to show a phenotypic correction and an improved clotting time. To increase huFVIII levels, an increased number of transduced epidermal stem cells can be employed.

EXAMPLE 3

The recent explosion in interest in stem cell research is due in large part to the recognition that a broad variety of adult tissues contain stem cells, and that these somatic stem cell populations may be pluripotent. At least they may be able to repopulate other adult tissues. However, there is no evidence that somatic stem cells are equivalent to embryonic stem cells. Epidermal stem cells appear to be true stem cells for adult skin in that they are self renewing, can recapitulate the epidermis, and can express a recombinant gene in the skin for long periods of time (Dunnwald, 2001). However, no one has evaluated them for embryonic functions.

Materials and Methods

Epidermal stem, TA, and total basal cells are isolated from back skin of C57BL/6-EGFP neonatal mice. 4-day C57BL/6 blastocysts are injected with 20 cells each of GFP-labeled epidermal stem, TA, or total basal cells. 15 blastocysts are transferred to each of 5 mothers for each cell type and for each harvest time [(5 mothers)×(3 cell types)×(3 harvest times)=30 mothers]. Embryos are harvested. Embryos are embedded then sectioned longitudinally at 10 µm, keeping every $10^{th}$ section. Sections are analyzed for GFP-expressing cells. The tissues and/or organs where GFP+ cells are found are morphologically identified. It is then determined if there is a difference between embryos developed with stem, TA, or total cells in number of surviving GFP+ cells and GFP+ cells are incorporated into tissues and organs. Percent survival (# developed embryos per # transferred) for each injected group is determined and compared to each other (by ANOVA) to determine if epidermal stem, TA or total cells inhibit implantation of blastocysts.

Sample Processing and Analysis

Embryos and neonates are either fixed in 4% paraformaldehyde and embedded in paraffin or cryoprotected in 30% sucrose, then frozen in O.C.T. compound for antibody analysis by immunofluorescence of sections. OCT freezing allows visualization of GFP and most antibodies will stain frozen sections, but the histology is not very good. If the neonatal bones are too calcified to section in either the paraffin embedded blocks or the O.C.T. blocks, a few selected internal organs (liver, stomach, heart, brain, spleen, and gonads), a piece of leg muscle, and a piece of back skin are dissected and embedded for antibody analysis.

Sections of embryos are deparafinized if necessary and examined for GFP-expressing cells using a Nikon Eclipse E600 microscope with epifluorescence. If only a few GFP+ cells are observed, then the number of GFP+ cells per area of tissue or organ is counted for each mouse at each time point. The slides of the tissues are projected, traced, then scanned into the computer, and the area measured using Image Pro software. The mean and standard error of # GFP+ cells per area is determined, and analysis of variance (ANOVA) performed to determine if there are significant differences among stem, TA, and total cells. A value of p<0.05 is taken to be a statistically significant result for this and all subsequent statistical analyses.

The EGFP gene can also be detected via PCR of each organ (see specific methods for details), which can be used to easily compare stem, TA, and total for amount of expression per organ and to determine if these cells contributed to the development of these organs, even though only a few cells showed expression of the EGFP gene. The bone marrow from the femurs and tibias can be aspirated to test for EGFP-expression in the hematopoietic system.

Results

Epidermal stem cells carrying the EGFP gene from transgenic mice in a C57BL/6 background (from Jackson Labs) were sorted. Twenty GFP-epidermal stem cells were injected into each of 15 4-day blastocysts. The blastocysts were transplanted to the uterus of a pseudopregnant C57BL/6 mother. Ten days later, embryos were harvested (development day E14), cryoprotected in 30% sucrose, frozen in O.C.T. compound, and sectioned longitudinally. GFP-labeled cells were present in the epidermis, as well as in several mesodermally-derived tissues, including liver, cartilage, and brain suggesting that epidermal stem cells can substitute for embryonic stem cells.

Preliminary data from tissues at E14 suggests that isolated somatic epidermal stem cells survive and proliferate after injection into blastocysts, and that they have the ability to incorporate into several tissues in fetal mice. If epidermal stem cells are truly pluripotent, they could provide an alternative to using embryonic stem cells as therapeutic treatment for disease.

EXAMPLE 4

To determine whether epidermal stem cells injected into blastocysts alter their phenotype during development, the following experiments are conducted. Epidermal stem cells, transient amplifying (TA), and total basal cells are isolated from the back skin of C57BL/6 neonatal mice which carry the EGFP gene (C57BL/6-EGFP), then injected into 4-day blastocysts from C57BL/6 mice that do not carry the EGFP gene. This allows the tracking of fluorescent GFP-labeled cells and the tissues that they form. The blastocysts are transferred to pseudopregnant C57BL/6 mothers and allowed to develop for an additional 6 (E10), 10 (E14), or 17 (birth) days in utero. Using histology, immunofluorescence, and expression of specific differentiation or lineage markers, the presence and contribution of GFP-marked epidermal stem cells to the formation of embryonic tissues and neonatal organs is evaluated. It is determined whether the GFP-marked cells retain their epidermal differentiation markers, or whether they have altered their phenotype and express tissue-specific markers, and whether the marked cells persist for the lifespan of the mouse.

Experimental Design

The mice and the general experimental design is the same as described in Example 3, except for analysis. GFP$^+$ cells are examined for expression of keratin K14 to determine if epidermal stem cells retain their epidermal distinction, then examined for expression of tissue-specific markers. The percentage of GFP$^+$ cells expressing K14, or other tissue-specific markers, is calculated, and differences among embryos developed with stem, TA, or total basal cells are compared.

For persistence studies, the mice are followed for at least 18 months or until near death, then tissues are harvested and analyzed for GFP-expressing cells and tissue-specific markers, beginning with hematopoietic and liver markers. The number of GFP$^+$ cells per area of tissue section is counted, and differences among embryos developed with stem, TA, or total basal cells is compared. It is determined if there is a difference between mice developed with stem, TA, or total cells in number of surviving GFP$^+$ cells per tissues or organs. The day of death is noted and length of survival compared among mice developed from blastocysts injected with stem, TA, or total cells. The controls are mice made from blastocysts that received no cells, and mice that were conceived normally. Survival for each group is compared to each other by ANOVA to determine if epidermal stem, TA or total cells are detrimental, beneficial, or have no effect on survival Sample Analysis Since a high percentage of GFP$^+$ cells are in the liver, and since liver is the primary hematopoietic cell producer during development, GFP$^+$ cells in the embryos are phenotyped first with antibodies to hematopoietic stem cells, second with antibodies to hematopoietic cell lineages, and third with tissue-specific markers, beginning with hepatocyte markers. For example, for epidermal stem, TA, and total cells; keratin 14 (Anti-K14 from Babco); bone marrow stem cell surface markers (all from Pharmagen); Sca-1 and c-Kit (CD 117); lack hematopoietic lineage-specific markers (Lin-); hematopoietic cell lineage markers (all from Pharmagen); B Lymphocytes: CD45R (B220); T lymphocytes: CD5 (Ly-1) or CD3, CD4, CD8; Erythroid cells: TER119; Granulocytes: Gr-1; Myelomonocytic cells: CD11b (Mac-1); liver; (Hepatocytes); cell—cell adhesion molecule (c-cam) (Accurate Chemical), epithelial junction marker, E-cadherin (Zymed), rabbit anti-albumin (Accurate Chemical), dipeptidyl peptidase IV/CD26 (PharMingen), alpha fetoprotein (fetal liver only) (Santa Cruz); brain; (Glial Cells) GFAP (Santa Cruz); heart; (actin (Santa Cruz); myosin (Santa Cruz); spleen; lymphocytes: CD45R (B220), CD5 (Ly-1) or CD3, CD4, CD8 (Pharmagen) and Macrophages: Mac-i (Pharmagen); stomach: E-cadherin (Zymed); K8/K18 (Sigma); actin (Santa Cruz); gonads: spectrin (Santa Cruz); muscle: actin (Santa Cruz); myosin (Santa Cruz); troponin (Santa Cruz); desmin (Santa Cruz); connective tissue; Fibroblasts: Vimentin (Sigma); and epithelium; E-cadherin (Zymed); K8/K18 (Sigma). Secondary antibodies are conjugated to streptavidin-Texas red so that immunolabeled cells and the GFP$^+$ cells can be visualized simultaneously using fluorescence or confocal microscopy. DAPI staining is used to delineate nuclei, and to count the total number of cells.

For persistence studies, tissues (epithelium, connective tissue, and leg muscle) and internal organs (liver, stomach, heart, brain, spleen, and gonads), are dissected, and bone marrow from the femurs and tibias aspirated from mice 18 months old, or mice as they near death. All tissues are fixed in 4% paraformaldehyde and embedded in paraffin or cryo-protected in 30% sucrose, then frozen in O.C.T. compound. Sections of each are analyzed for GFP-expressing cells and for tissue-specific antibody expression. The number of GFP$^+$ cells per area of each tissue is counted for each mouse at each time point, and compared to the counts/area obtained for embryonic and neonatal tissues. For life span determination, a group of 5 mice each (stem-injected, TA-injected, total-injected, and a normally born control) is allowed to live out their normal life span. Survival rates for each group are compared by analysis of variance (ANOVA).

Results and Discussion

Based upon preliminary data, GFP$^+$ cells are likely in the developing embryos that received epidermal stem cells and in most, if not all, of the tissues and organs. If the mice developed from epidermal stem cell injection have normal tissues and organs that show no difference in function and live normal life spans, this suggests that epidermal stem cells can substitute for embryonic stem cells and that the skin may be a source of generic stem cells or a substitute for replacement cells in a disease model, e.g., liver regeneration.

EXAMPLE 5

The cell cycle is an ordered, sequential process that leads to proper duplication and separation of the chromosomes into two new daughter cells. During the four phases of the cell cycle, cyclins, cyclin-dependent kinases and their inhibitors are the major players to phosphorylate substrate to allow the cell cycle progression. The phosphorylation of the retinoblastoma protein (pRb) family (which includes pRb, p107 and p130) and its dissociation from transcription factors leads to its inactivation and constitutes the key process to the progression into the cycle.

Many studies have examined cell cycle modifications in terminal differentiation-associated growth arrest, apoptosis or cancer. In keratinocytes, cell differentiation leads to increase level of cyclin-dependent kinase inhibitor and mice lacking p21 were more susceptible to chemically induced skin carcinoma. Interestingly, primary keratinocytes derived from these animals showed an increased proliferative potential. All these studies examined cell cycle protein regulation in relation to terminal differentiation. However, none of them focused on early differentiation, i.e. stem cells vs. transient amplifying cells.

As described below, epidermal stem cells are cycling and not held out of the cell cycle. Furthermore, their cell cycle profile is an intrinsic property and does not depend on the age of the donor nor the proliferative state of the tissue that they maintain.

Material and Methods

Cell Isolation

Ears and footpads from adult mice (8–14 weeks old) as well as neonate (1–2 days old) back skin were isolated and incubated in Dispase II (Boehringer-Mannheim, Germany) overnight at 4° C. The epidermis was mechanically separated from the dermis and placed in trypsin 0.25% (Life Technologies, Rockville, Mass.) for 30 minutes at 37° C.; basal epidermal cells were dissociated by gently shaking the epidermis in low calcium culture medium (SMEM (Life Technologies), 7% chelexed fetal calf serum (Life Technologies), 1% penicillin/streptavidin/amphotericinB (Life Technologies), 0.06M $CaCl_2$). Cells were resuspended in Hoechst 33342 (Sigma, St-Louis, Mo.) and propidium iodide solution (Sigma) to separate the stem cells from the transient amplifying cells as previously described (Dunnwald, 2001). A slight modification was made in the Hoechst 33342 preparation, by dissolving the Hoechst powder in water and keeping the stock at −80° C. until use. To insure that the sorting parameters were standard, 25% of the smallest cells from the total population were collected. Selection of the stem cells was performed according to their dye characteristics as described in Dunnwald (2001). Transient amplifying cells were obtained by selecting larger cells unrespectively of their dye content.

Cell Cycle Analysis

Cell cycle profiles of sorted adult mouse stem and transient amplifying cells from footpad and ear, and neonate back skin control were determined. Keratinocytes were centrifuged and resuspended at $5 \times 10^5$ cells/ml in a hypotonic propidium iodide solution (1 mM Tris, 0.1 mM EDTA, 0.1% Triton-X100, 3.4 mM Na Citrate, 0.05 mg propidium iodide). The cells were allowed to sit in the stain on ice for at least 15 minutes before processing through the FACScan (Becton-Dickenson) flow cytometer. DNA content was measured using an excitation wavelength of 488 nm and an emission wavelength of 455 nm, and analyzed using the CellQuest® v3.2 software program (Becton-Dickenson), and graphed with ModFit LT v2.0 software (Verity Software House, Inc.).

BrdU Incorporation

Sorted neonate and adult mouse stem and transient amplifying cells were incubated for 1 hour at 37° C. with a solution of 200 µg/ml 5-Bromo-2'-Deoxyuridine-5'-triphosphate (BrdU, Sigma). Cells were spread on a glass slide and fixed in cold 70% EtOH. After denaturing the DNA with 2N HCl for 30 minutes, cells were washed with PBS and incubated with a FITC-conjugated anti-BrdU antibody (Beckton-Dickinson, San Jose, Calif.) overnight at room temperature. Coverslips were mounted with Prolong® (Molecular Probe, Eugene, Oreg.) and observed under a Nikon epifluorescent microscope. At least 1000 cells were counted in three individual fields for each experiment. The number of BrdU expressing cells was determined and the percentage of positive cells calculated by dividing the number of BrdU positive cells by the total number of counted cells.

Immunostaining

Sorted neonate and adult mouse stem and transient amplifying cells were fixed in 70% ethanol for 10 minutes at 4° C. They were incubated with an anti-cyclin B1 monoclonal antibody (1/50; Pharmingen, San Diego, Calif.) for one hour and then with FITC-conjugated goat anti-mouse IgG (1/100; Sigma) for 30 minutes. Cell nuclei were labeled with DAPI after immunofluorescence staining. At the end of the procedure, the cells were spread on slides, dried, and mounted with Prolong® (Molecular Probe) before observations under an epifluorescent Nikon microscope. The percentage of positive cells was then determined.

Results

A Standardized Sorting Method Yields More Stem Cells in Mouse Neonate Epidermis as Compared to Adult Cells were sorted using a Coulter Epics 753 according to their size (forward and side scatter (FIG. 7A, and their dye characteristics (Hoechst blue and red, FIGS. 7B and C). TA cells were obtained without regard of dye nor size characteristics. The space between the "A" and "B" boxes was designed to avoid any overlap or contamination from one population to the other.

The "A" box to contain 25% of the cell population, however, because of biological variations, the range varied from 14 to 32% (21.6±1.66, n=11; mean±SEM). Within this population, the stem cells were collected based on their low blue and low red Hoechst characteristics. The TA cells were contained in the "B" box, which corresponded to larger cells than the stem cells. This first size selection was important since TA cells also exhibited low blue and red Hoechst characteristics. Using this method, neonate back skin and adult ear and footpad were sorted into stem cells and TA cells. It was found that 8.4% of the basal cells were stem cells in neonate back skin. Only 3.7 and 3.8% of basal cells in adult ear and adult footpad respectively were stem cells (Table 3). These numbers showed more than a two-fold difference in the amount of stem cells between adult and neonate.

TABLE 3

| Percentage of stem cells in mouse epidermis[a] | | |
|---|---|---|
| Neonate back skin (n = 12) | Adult ear (n = 8) | Adult footpad (n = 7) |
| 8.39 ± 0.54*** | 3.7 ± 0.41[b] | 3.83 ± 0.34[b] |

[a]Values are means ± SEM
[b]Not statistically different than adult footpad
***$p < 0.001$ when comparing with both adult ear and adult footpad with t-test.

The Cell Cycle Profile of Adult Stem Cells is An Intrinsic Property of the Stem Cells In order to evaluate the cell cycle properties of the sorted stem cells and TA cells, a cell cycle profile was established by FACS analysis for each of the isolated populations. In all the groups of cells evaluated (adult and neonate stem cells and TA cells), the vast majority was held in the G0/G1 phase of the cell cycle, as it would be expected from a freshly isolated cell population (FIG. 8, Table 4).

TABLE 4

Cell cycle analysis of sorted neonate and adult mouse epidermal keratinocytes[a]

|    | Neonate back skin | | Adult ear | | Adult footpad | |
|----|---|---|---|---|---|---|
|    | G0/G1 | S-G2/M | G0/G1 | S-G2/M | G0/G1 | S-G2/M |
| TA | 85.6 ± 2.69 | 14.3 ± 2.69 | 93.7 ± 0.63 | 6.3 ± 0.62 | 85.0 ± 1.91 | 15 ± 1.91 |
|    | (n = 6) | | (n = 9) | | (n = 6) | |
| SC | 96.2 ± 0.77 | 3.8 ± 0.77 | 97.4 ± 0.59 | 2.6 ± 0.59 | 94.7 ± 1.67 | 5.3 ± 1.67 |
|    | (n = 7) | | (n = 7) | | (n = 5) | |

[a]Data are means ± SEM

However, the profiles show major differences in the proportion of dividing cells. In all the cells examined (neonate, adult footpad, adult ear), the proportion of stem cells dividing varied from 2.6% (adult ear) to 3.8% (neonate back skin) and 5.3% (adult footpad), without any statistical differences (Table 4). However, major differences in the percentage of cells in the S-G2/M phase of the cell cycle was found in the TA cell population. In neonate back skin and adult footpad, 15% of the TA cells were dividing, whereas only 6.3% of the TA cells in adult ear were in the S-G2/M phase of the cell cycle. In other words, the cell cycle profile of TA cells clearly showed a higher proportion of dividing cells in proliferative tissues (adult footpad and neonate back skin) compared to normal mouse epidermis (adult ear). Thus, these data show quantitatively that the cell cycle profile of adult TA cells is dependent of the proliferative state of the tissue they maintain, whereas the cell cycle profile of stem cells is their intrinsic property.

The Stem Cells are Dividing

The question as whether the stem cells are cycling or held out of the cell cycle has been a matter of debate for many years. To answer that question, sorted mouse stem cells and TA cells were incubated in BrdU for 1 hour at 37° C. During that time, any cell synthesizing DNA (in S phase of the cell cycle) will incorporate BrdU which can be detected by immunostaining. Neonate as well as adult mouse ear and footpad stem cells showed BrdU staining after an hour pulse. Positive cells were counted in each population and percentage of sorted cells was calculated (Table 5).

TABLE 5

Percentage of BrdU positive cells in sorted neonate and adult mouse epidermal keratinocytes[a]

|    | Neonate back skin (n = 4) | Adult ear (n = 3) | Adult footpad (n = 3) |
|----|---|---|---|
| TA | 6.0 ± 0.55[b] | 2.1 ± 0.67[b] | 3.6 ± 0.62[b] |
| SC | 1.3 ± 0.25 | 0.3 ± 0.06 | 0.9 ± 0.33 |

[a]Data are means of means ± SEM
[b]p < 0.001 vs. all other TA groups, p < 0.05 vs. all stem cell groups after one-way non parametric ANOVA and Newman-Keuls as post hoc test.

It was found that 0.3% of adult ear stem cells and 0.9% of adult footpad stem cells positive for BrdU (not statistically different), whereas 2.1% and 3.6% TA cells from adult ear and adult footpad respectively showed BrdU positivity. Neonate control was 1.3% for the stem cells and 6% for the TA cells. These results indicate that stem cells are going through the S phase of the cell cycle and that the TA cells are dividing at a higher rate than the stem cells.

To confirm that the sorted stem cell populations were proceeding through G2 and M, cyclin B1 immunostaining was performed. Cyclin B1 is specifically expressed at the end of G2 and during mitosis. Its degradation via the ubiquitination pathway is one of the trigger to exit mitosis. Cyclin B1 expression was detected in all the sorted population. The percentage of positive cells varied from 0.17% to 0.21% in all stem cells and TA cells respectively (not statistically different). Taken together, these results clearly demonstrated that stem cells are dividing and are not held out of the cell cycle.

Discussion

This study was undertaken to better understand the cell cycle properties of epidermal stem cells. It was known for a long time that a subset of cells within the interfollicular epidermis was able to retain nuclear label for a long period of time. This property has been the foundation for the characterization of stem cells, and lead to the conclusion that stem cells were slowly cycling. However, no data on their cell cycle properties was available since isolation a pure population of epidermal stem cells was problematic. A new sorting method which allowed the sorting of stem cells from transient amplifying (TA) cells was available (Example 1) which was slightly modified by first gating cells according to their size. This results in a better separation since both stem and TA cells have a low Hoechst content. This similar dye content in epidermal cells is in contrast with hematopoietic, and muscle stem cells, which all exhibit differential Hoechst blue and red content.

It is commonly believed that stem cells are quiescent in normal steady state, and that this phenomenon plays an important role in the preservation of stem cells function and potentiality. However, this does not mean that stem cells are dormant. Hematopoietic stem cells divide on average every 30 to 57 days and label-retaining studies performed in skin suggest that some epidermal cells take at least 30 days to divide. In the hair follicle, Morris et al. (1999) showed that some cells could even retain the label for 14 months. The cell cycle profile of sorted stem cells from adult and neonate showed that about 3% of the stem cells were dividing. This percentage is similar to what Tani et al. (2000) reported with an enriched $\alpha 6^{bri}CD71^{dim}$ adult mouse epidermal cell population. In the hematopoietic system, another continuously renewing tissue, there is also 3% of adult mouse stem cells that are dividing. Moreover, the results described herein show that the cell cycle profile of the stem cells is independent of the age of the donor, nor the tissue they maintain. Thus, the consistency in the percentage of stem cells dividing demonstrates that the cell cycle profile is an intrinsic characteristic of these cells. The stem cells seems to be programmed at birth to cycle at a define rate to maintain the homeostasis of the tissue, and this property is common to at least two major renewing tissues, skin and blood.

A number of properties are frequently ascribed to stem cells, one of them being the ability to undergo asymmetric cell division. When a stem cell divides, it produces two daughter cells: a stem cell in order to preserve the pool of stem cells, and a more differentiated cell that is committed to differentiation commonly named "transient amplifying cell". These cells are a transit population of proliferating cells situated between the stem cells and the mature functional compartment, i.e., cells between the basal layer and the subsequent suprabasal layers of the epidermis. The cell cycle analysis described above shows that transient amplifying cells are dividing at a higher rate compared to the stem cells. The data also show a difference in the cell cycle profile within the TA cell compartments; TA cells from neonate back skin and adult footpad have a higher rate of division compared to TA cells from adult ear. It is known from morphological analysis that the thickness of the ear epidermis is thinner than adult footpad and neonate back skin. Furthermore, the labeling index is higher in adult footpad compared to adult ear. Therefore, the results indicate that there is a direct correlation between the thickness of the epidermis, its proliferative status and the cell cycle profile of the TA. Thus, the TA cells of a given epidermis are responsible for the number of cell layers it contains. Their cell cycle profile could be used as an indicator of the proliferative status of the tissue.

Progress from one phase of the cell cycle to the next is controlled by activation or inactivation of cyclin-dependent kinases. A cascade of event lead to the phosphorylation of pRb and its family members and the progression of the cell through S, than G2 and finally M. Variations in the length of the cell cycle are primarily due to variations in the length of two gap phases, whereas DNA synthesis and mitosis are more constant. The results described herein show differences in the amount of BrdU positive cells after an hour of pulse between stem cells and TA cells. However, no difference could be detected in the proportion of cyclin B1 positive cells in each group. Cyclin B1 is a marker for mitosis, which is the shortest phase of the cell cycle (about one hour). It is difficult to detect differences within a short period of time, which is likely to be the reason of the similar results between each group. Thus, the difference in the length of the cell cycle between stem cells and TA cells likely resides in the G1 phase.

Do newborns have more stem cells than adults? According to the results described herein, the answer to this long-standing question in the field of skin biology is yes. Already fifty years ago, clinical observations from wound healing and burn patients showed that young individuals healed faster than older ones. In culture, newborn foreskin keratinocytes can undergo a higher number of passages as compared to adult. Previously it had been hypothesized that the lifespan of these cultures was depending on the number of stem cells initially present, which suggests that young individuals have more stem cells than adults. Using the sorting method to isolate stem cells, a two-fold difference in the amount of stem cells between neonate and adult was found. This result confirms the idea that the younger an organism is, the more stem cells and more proliferative potential it has.

In conclusion, it was shown that the cell cycle profile of mouse epidermal stem cells is independent of the age of the donor and the tissue they maintain, whereas the cell cycle profile of TA cells could be used as an indicator of the proliferative status of the epidermis. One question remains unanswered: why are stem cells cycling at a slower rate than TA? Stem cells have been shown to be "stickier" than the TA cells (Bickenbach, 1998). Several studies have reported anchorage-dependent cell cycle regulation, and non-transformed cells cultured in suspension fail to undergo DNA synthesis and differentiate, i.e. basal keratinocytes grown in methylcellulose express involucrin. Therefore, the fact that stem cells may be more anchored to the basement membrane than other cells in the basal layer could prevent them from cycling at a high rate. External signals could also be responsible for the cell cycle properties of the stem cells. Many reports suggest the importance of neighboring cells in the fate of stem cells, from the Drosophila ovary to the Arabidopsis shoot meristem. In the epidermis, Delta 1 expression by epidermal 1 bright cells could have a protective effect on stem cell properties by blocking Notch signaling. Finally, the cell cycle is a big machinery with many players involved. Preliminary data suggest that the level of cyclin D1, cyclin E, cyclin A, and p27 were similar between stem and TA cells obtained from neonate back skin (data not shown). However, functional analysis need to be performed in order to elucidate the mechanisms underlying the discrepancy between stem and TA cell cycle characteristics.

REFERENCES

Barrandon Y et al., *Proc Natl Acad Sci USA*, 82, 5390–5394 (1985).
Barrandon Y et al., *Proc Natl Acad Sci USA*, 84, 2302–2306 (1986).
Bernstein I D et al., Blood Cells, 20, 15–23 (1994).
Bickenbach J R, *J Dent Res,*. 122C, 1611–1620 (1981).
Bickenbach J R et al., *J Invest Dermatol*, 82, 618–622 (1984).
Bickenbach J R et al., *Cell Tissue Kinet*, 19, 325–333 (1986).
Bickenbach J R et al., *J Invest Dermatol*, 88, 42–46 (1987).
Bickenbach J R, Selection and growth of epidermal stem cells, in *Bioengineering of Skin Substitutes*, L. M. Savage, Editor, IBC Library Series: Southborough, Mass. p. 75–92 (1998).
Bickenbach J R et al., *Exp Cell Res*, 244, 184–195 (1998).
Bickenbach et al., *Proc Assoc Amer Physicians* 111, 184–189 (1999).
Brill S et al., *Proc Soc Exp Biol Med*, 204, 261–269 (1993).
Cairnie A B et al., Stem cells of renewing populations, New York, Academic Press (1976).
Cairns J, *Nature* 255, 197–200 (1975).
Choate K A et al., *Hum Gene Ther*, 7, 2247–2253 (1996).
Choate K A et al., *Human Gene Therapy*, 8, 895–901 (1997).
Chung S Y et al., *Mol Cell Diff* 2, 61–81 (1994).
Compton C C et al., *Lab Invest*, 60, 600–612 (1989).
Cosset F L et al., *J Virol*, 69, 7430–7436 (1995).
Cotsarelis G et al., *Cell*, 57, 201–209 (1989).
Cotsarelis G et al., *Cell*, 61, 1329–1337 (1990).
Dellambra E et al., *Human Gene Therapy*, 9, 1359–1370 (1998).
De Luca M et al., *Burns*, 15, 303–309 (1989).
Deng H et al., *Nature Biotech*, 15, 1388–1391 (1997).
Dunnwald et al., *Exp. Dermat.*, 10:45 (2001)
Durand B et al., *Blood*, 84, 3667–3674 (1994).
Fakharzadeh S S et al., *Blood*, 95, 2799–2805 (2000).
Fenjives E S et al., *J Invest Dermatol*, 106, 576–578 (1996).
Flowers M E D et al., *Proc Natl Acad Sci USA* 87, 2349–2353 (1990).
Freiberg R A et al., *Hum Mol Genet*, 6, 927–933 (1997).
Fuchs E, *J Cell Biol*, 111, 2807–2814 (1990).
Garlick J A et al., *J Invest Dermatol*, 97, 824–829 (1991).
Gelfant S, *J Invest Dermatol*, 78, 296–299 (1982).
Ghazizadeh S et al., *Gene Therapy*, 6, 1267–1275 (1999).
Goodell M A et al., *J Exp Med*. 183, 1797–1806 (1996).
Gothot A et al., *Blood*, 90, 4384–4393 (1997).
Hager B et al., *J Invest Dermatol*, 112, 971–976 (1999).
Hayat M A, Basic Electron Microscopy Techniques, New York, Van Nostrand Reinhold Co. (1972).
Hayflick L, *Exp Cell Res*, 37, 614–636 (1965).

Hoeben R C et al., *J Biol Chem*, 265, 7318–7323 (1990).
Huber T S et al., *J Vasc Surg*, 22, 795–803 (1995).
Jackson K A et al., *Proc Natl Acad Sci*, 96, 14482–14486 (1999).
Jones P H et al., *Cell*, 73, 713–724 (1993).
Jones P H et al., *Cell* 80 83–93 (1995).
Karnovsky M J, *J Cell Biol*, 27, 137A–138A (1965).
Kitten 0 et al., *Hum Gene Ther*, 10 1491–1494 (1997).
Kolodka T M et al., *Proc Natl Acad Sci USA*, 95, 4356–4361 (1998).
Lajtha G, *Differentiation*, 14, 23–34 (1979).
Lavker R M et al., *Science*, 215, 1239–1241 (1982).
Li A et al., *Proc Natl Acad Sci USA*, 95, 3902–3907 (1998).
Lyle S et al., *J Cell Sci*, 111, 3179–3188 (1998).
Mackenzie I C et al., *Cell Tissue Res*, 235, 551–559 (1984).
Mackenzie I C et al., *Differentiation*, 41, 127–138 (1989).
Mackenzie I C et al., *Epith Cell Biol*, 2, 107–119 (1993).
Mackenzie I C, *J Invest Dermatol*, 109, 377–383 (1997).
Michel M et al., *J Cell Sci*, 109, 1017–1028 (1996).
Morgan J R et al., *Science*, 237, 1476–1479 (1987).
Morris R J et al., *J Invest Dermatol*, 112, 470–475 (1999).
Otto W R et al., *Plast Reconstr Surg*, 96, 166–176 (1993).
Pavlovitch J H et al., *Am J Physiol (Cell Physiol* 30), 261, C964–C972 (1991).
Potten C S, Stem Cells, London: Academic Press (1997).
Rheinwald et al., *Cell*, 6, 331–344 (1975).
Sanes J R, *Trends Neurosci*, 12, 21–28 (1989).
Seitz C S et al., *Gene Ther*, 6, 42–47 (1999).
Spangrude G J et al., *Science*, 241, 58–62 (1988).
Veer Reddy G P et al., *Blood*, 90, 2293–2299 (1997).
Waseem A et al., *J Invest Dermatol*, 112, 362–369 (1999).
Whitbread L A et al., *Exp Cell Res*, 244, 448–459 (1998).
Vogt P M et al., *Proc Natl Acad Sci USA*, 91, 9307–9311 (1994).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerable without departing from the basic principles of the invention.

What is claimed is:

1. A method to prepare isolated mammalian epidermal stein cells, comprising:
   (a) providing a sample comprising mammalian epidermal stem cells obtained from mammalian epidermal tissue, which sample is contacted with an agent that binds DNA in viable cells and an agent that binds non-viable cells;
   (b) separating the sample into a first population of cells that are the smallest 30% of the viable cells in the sample and a second population of cells that are larger than the cells in the first population, wherein the first population comprises a substantially pure population of epidermal stem cells; and
   (c) isolating a substantially pure population of epidermal stem cells from the first population of epidermal stem cells.

2. A method to prepare isolated mammalian epidermal stem cells, comprising:
   (a) providing a sample comprising mammalian epidermal stem cells obtained from mammalian epidermal tissue, which sample is contacted with a dye with low or no cellular toxicity that binds DNA in viable cells and an agent that binds non-viable cells;
   (b) separating the sample into a first population of cells that are the smallest 30% of the viable cells in the sample and a second population of cells that are larger than the cells in the first population, wherein the first population comprises a substantially pure population of epidermal stem cells; and
   (c) isolating a substantially pure population of epidermal stem cells from the smaller cells.

3. The method of claim 1 or 2 wherein the mammalian cells are murine cells.

4. The method of claim 1 or 2 wherein the mammalian cells are human cells.

5. The method of claim 1 or 2 wherein the mammalian cells are primate cells.

6. The method of claim 1 or 2 wherein the sample comprises mammalian epidermal cells which have been dissociated from non-epidermal cells.

7. The method of claim 1 or 2 wherein the agent which binds DNA is a Hoechst dye.

8. The method of claim 7 wherein the dye is Hoechst 33342.

9. The method of claim 1 or 2 wherein the agent that binds non-viable cells is propidium iodide.

10. The method of claim 7 wherein the agent that binds non-viable cells is propidium iodide.

11. The method of claim 1 or 2 wherein the separation is performed with a flow cytometer.

12. The method of claim 1 or 2 wherein the sample is in a medium which lacks azide.

13. The method of claim 1 or 2 wherein the sample is further contacted with a nuclear-retained label prior to separation.

14. The method of claim 1 or 2 wherein the cells in the second population have proliferative capacity.

15. A method to prepare mammalian epidermal stem cells, comprising:
   (a) contacting a population of mammalian epidermal cells comprising epidermal stem cells with an amount of a first agent under conditions effective for viable cells to retain the first agent, wherein the mammalian epidermal cells are obtained from mammalian epidermal tissue;
   (b) contacting the population of (a) with an amount of a second agent under conditions effective for non-viable cells to retain the second agent; and
   (c) separating the population of(b) into a first population of cells which first population represents the smallest 30% of the viable cells which comprise viable epidermal stem cells and a second population of cells which represents larger cells, which second population does not comprise a substantial portion of epidermal stem cells.

16. The method of claim 15 further comprising isolating the epidermal stem cells.

17. The method of claim 15 wherein the mammalian cells are murine cells.

18. The method of claim 15 wherein the mammalian cells are human cells.

19. The method of claim 15 wherein the mammalian cells are primate cells.

20. The method of claim 15 wherein the sample comprises mammalian epidermal cells which have been dissociated from non-epidermal cells.

21. The method of claim 15 wherein the first agent is a Hoechst dye.

22. The method of claim 21 wherein the dye is Hoechst 33342.

23. The method of claim 15 wherein the second agent is propidium iodide.

24. The method of claim 15 wherein the sample is further contacted with a nuclear-retained label prior to separation.

25. The method of claim 15 wherein the cells in the second population have proliferative capacity.

26. A method to prepare a substantially pure population of mammalian epidermal stem cells, comprising: separating a sample obtained from mammalian epidermal tissue which comprises mammalian epidermal stem cells and epidermal cells which are not epidermal stem cells and contacted with a Hoechst dye and propidium iodine or pyronidine iodine, into a substantially pure population of epidermal stem cells which comprise the hoechst dye but not propidium iodine or pyronidine iodine and into at least one population of cells that does not comprise a substantial portion of epidermal stem cells.

27. A method to prepare mammalian epidermal stem cells, comprising:
   separating a sample obtained from mammalian epidermal tissue which comprises mammalian epidermal stem cells and epidermal cells which are not epidermal stem cells and contacted with a Hoechst dye and propidium iodine or pyronidine iodine, into a population which represents the smallest 30% of the viable cells in the sample and into a population which comprises larger cells, wherein the population with the smallest 30% of the viable cells comprises a substantially pure population of epidermal stem cells which comprise the Hoechst dye but not propidium iodine or pyronidine iodine.

28. A method comprising:
(a) providing a sample comprising mammalian epidermal stem cells obtained from mammalian epidermal tissue, which sample is contacted with an agent that binds DNA in viable cells and an agent that binds non-viable cells; and
(b) separating the sample into a first population of cells that are the smallest 30% of the viable cells in the sample and a second population of cells that are larger than the cells in the first population, wherein the first population comprises a substantially pure population of epidermal stem cells.

29. A method comprising:
(a) providing a sample comprising mammalian epidermal stem cells obtained from mammalian epidermal tissue, which sample is contacted with a dye with low or no cellular toxicity that binds DNA in viable cells and an agent that binds non-viable cells; and
(b) separating the sample into a first population of cells that are the smallest 30% of the viable cells in the sample and a second population of cells that are larger than the cells in the first population, wherein the first population comprises a substantially pure population of epidermal stem cells.

* * * * *

UNITED STATES PATENT AND TRADEMARK OFFICE
CERTIFICATE OF CORRECTION

PATENT NO. : 6,927,060 B2
DATED : August 9, 2005
INVENTOR(S) : Bickenbach et al.

It is certified that error appears in the above-identified patent and that said Letters Patent is hereby corrected as shown below:

Column 13,
Line 56, delete "run" and insert -- nm --, therefor.

Column 14,
Line 40, delete "$1 \times 10^{104}$" and insert -- $1 \times 10^4$ --, therefor.

Column 17,
Lines 56-57, below "VIII" delete "Coamatic®" (first occurrence) and insert
-- Coamatic® -- (as heading), therefor.

Column 29,
Line 8, delete "0" and insert -- O --, therefor.
Line 8, after "10" insert -- , --.

Column 31,
Line 11, delete "stein" and insert -- stem --, therefor.

Signed and Sealed this

Eighth Day of November, 2005

JON W. DUDAS
*Director of the United States Patent and Trademark Office*